United States Patent
Scherer et al.

(10) Patent No.: US 9,518,917 B2
(45) Date of Patent: Dec. 13, 2016

(54) MID-INFRARED HYPERSPECTRAL SPECTROSCOPY SYSTEMS AND METHODS THEREFOR

(71) Applicant: California Institute of Technology, Pasadena, CA (US)

(72) Inventors: Axel Scherer, Barnard, VT (US); Frank T. Hartley, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/065,792

(22) Filed: Mar. 9, 2016

(65) Prior Publication Data
US 2016/0266035 A1 Sep. 15, 2016

Related U.S. Application Data

(60) Provisional application No. 62/130,357, filed on Mar. 9, 2015, provisional application No. 62/235,687, filed (Continued)

(51) Int. Cl.
*G01N 21/35* (2014.01)
*G01J 3/42* (2006.01)
(Continued)

(52) U.S. Cl.
CPC ......... *G01N 21/3577* (2013.01); *G01J 3/2803* (2013.01); *G01J 3/42* (2013.01)

(58) Field of Classification Search
CPC .................. G01N 21/3577; G01J 3/2803
See application file for complete search history.

(56) References Cited

U.S. PATENT DOCUMENTS 5,550,373 A * 8/1996 Cole .................. G01J 3/02
                                                    250/338.1
5,674,457 A 10/1997 Williamsson et al.
(Continued)

FOREIGN PATENT DOCUMENTS

WO        2015003759 A1    1/2015

OTHER PUBLICATIONS

Authorized Officer: Sung Chul Kang, "International Search Report" issued in counterpart International Patent Application No. PCT/US2016/021629, dated Jun. 17, 2016, Publisher: PCT, Published in: WO.

*Primary Examiner* — Casey Bryant
(74) *Attorney, Agent, or Firm* — Kaplan Breyer Schwarz & Ottesen, LLP

(57) ABSTRACT

MIR spectroscopy systems comprising hierarchical spectral dispersion that enables fine spectral resolution and high sensitivity spectroscopy are disclosed. Hierarchical spectral dispersion is derived by employing at least two diffractive lens arrays, located on either side of a test sample, each receiving input radiation having an input spectral range and distributing the input radiation into a plurality of output signals, each having a fraction of the spectral range of the input radiation. As a result, the signal multiplication factor of the two arrays is multiplied in a manner that mitigates the propagation of wavelength harmonics through the system. In some embodiments, an emitter array comprising a plurality of spectrally selective emitters provides the input MIR radiation to a spectroscopy system. In some embodiments, spectrally selective detectors are used to detect narrow spectral components in the radiation after they have passed through the test sample.

30 Claims, 11 Drawing Sheets

Related U.S. Application Data on Oct. 1, 2015, provisional application No. 62/264,752, filed on Dec. 8, 2015.

(51) Int. Cl.
*G01N 21/3577* (2014.01)
*G01J 3/28* (2006.01)

(56) References Cited

U.S. PATENT DOCUMENTS

| | | |
|---|---|---|
| 5,801,057 A | 9/1998 | Smart et al. |
| 2002/0033453 A1 | 3/2002 | Sauer et al. |
| 2003/0171696 A1 | 9/2003 | Dosmann |
| 2003/0212346 A1 | 11/2003 | Yuzhakov et al. |
| 2008/0094620 A1 | 4/2008 | Li et al. |
| 2010/0032298 A1 | 2/2010 | Reel et al. |
| 2010/0097613 A1 | 4/2010 | Saari |
| 2012/0122084 A1 | 5/2012 | Wagner et al. |
| 2012/0307081 A1* | 12/2012 | Dewald .......... G01J 3/10 348/207.11 |
| 2014/0219886 A1 | 8/2014 | Choi et al. |
| 2014/0253714 A1* | 9/2014 | Weida .......... G02B 21/088 348/80 |
| 2014/0268127 A1 | 9/2014 | Day |

* cited by examiner

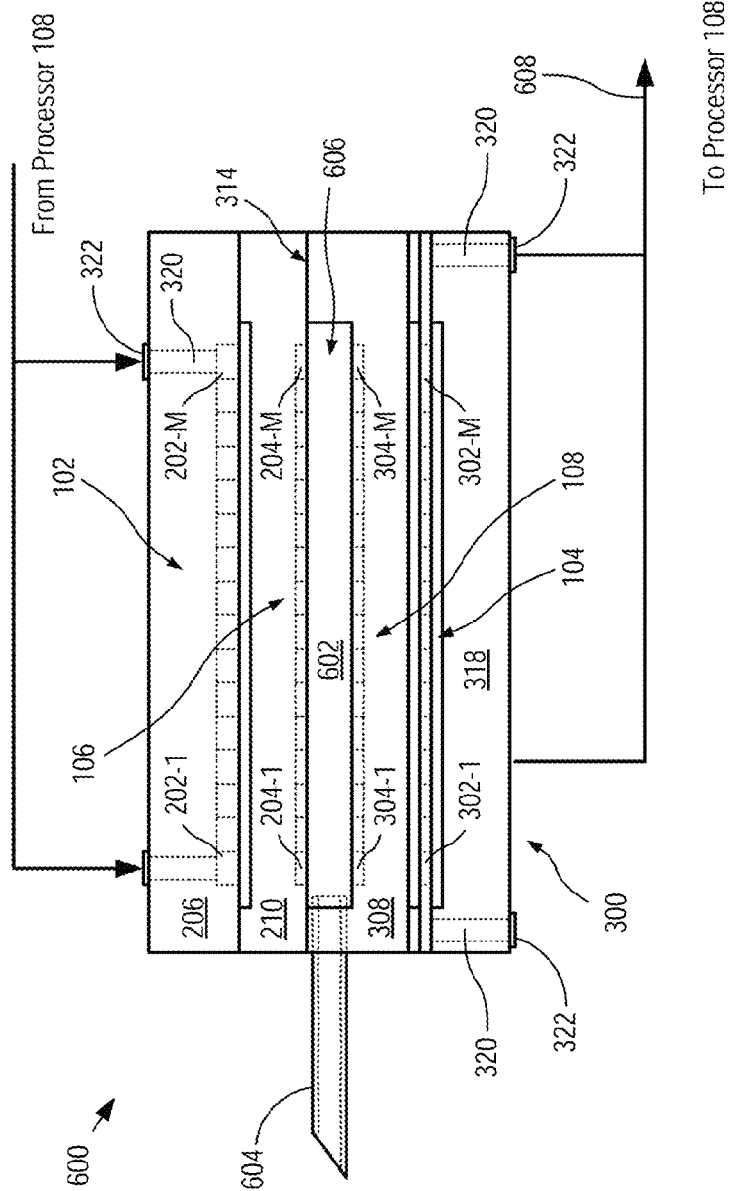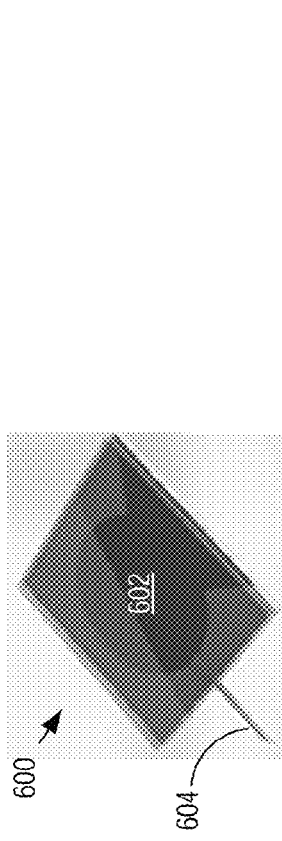
FIG. 6A
FIG. 6B

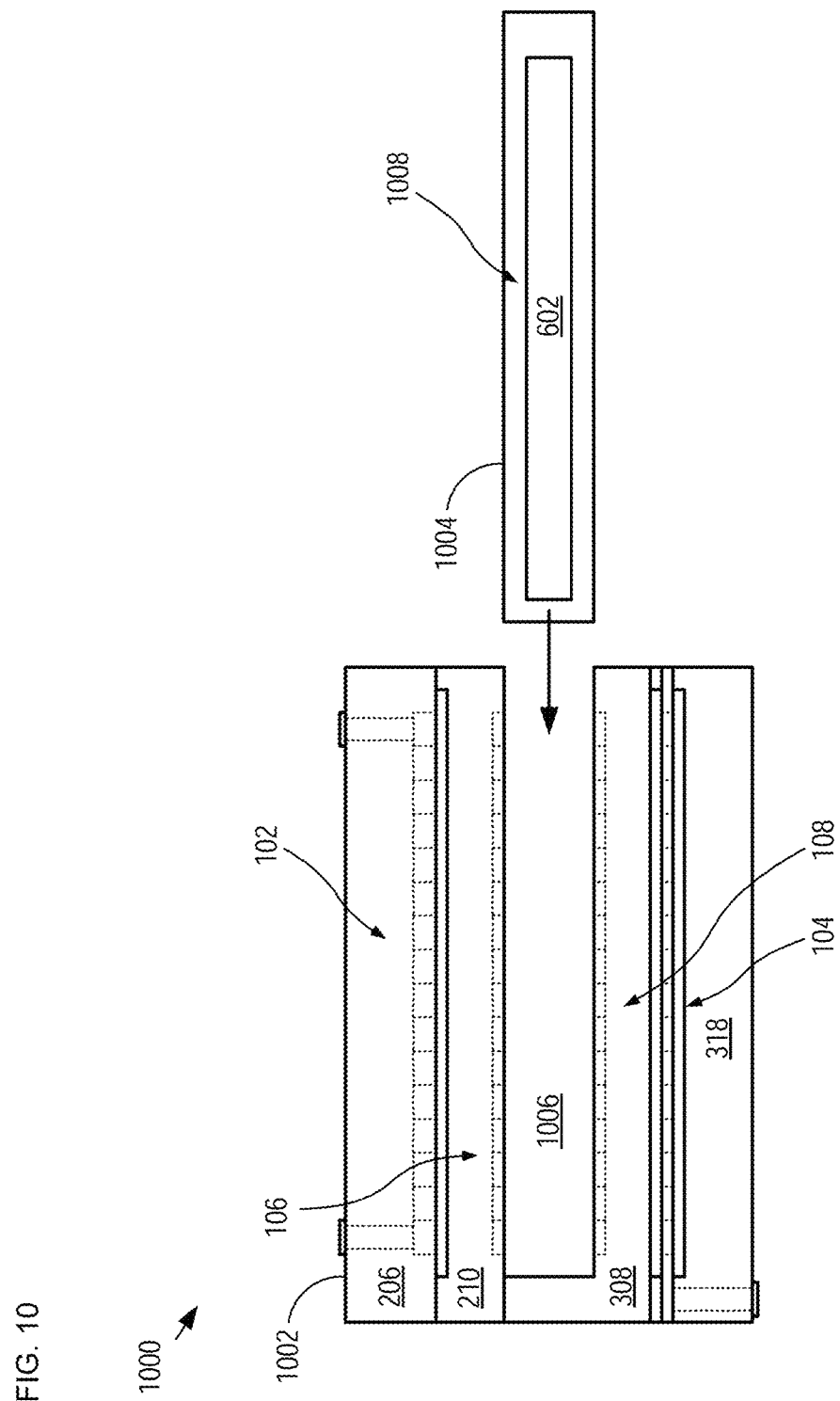

ID-INFRARED HYPERSPECTRAL
SPECTROSCOPY SYSTEMS AND METHODS
THEREFOR

CROSS REFERENCE TO RELATED
APPLICATIONS

This case claims priority of U.S. Provisional Patent Application Ser. No. 62/130,357, filed Mar. 9, 2015, U.S. Provisional Patent Application Ser. No. 62/235,687, filed Oct. 1, 2015, and U.S. Provisional Patent Application Ser. No. 62/264,752, filed Dec. 8, 2015, each of which is incorporated by reference. If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to systems and methods for hyperspectral spectroscopy and, more particularly, to hyperspectral spectroscopy in the mid-infrared wavelength range.

BACKGROUND OF THE INVENTION

Infrared spectroscopy is a technique for analyzing the chemical makeup of a sample and is widely used in many applications, such as medical diagnostics, petroleum exploration, environmental health monitoring, and drug testing.

Identifying and quantifying the chemical makeup of a test sample spectroscopically is enabled by the fact that atoms are not held rigidly apart in a molecule. Instead, they can move, as if they are attached by a spring that can bend and stretch. If a bond between a pair of atoms is subjected to radiation of a particular energy, it can absorb the energy and the bond can move from a first vibrational state to the next higher vibrational state. The specific wavelengths at which such absorption takes place is determined by the shape of the molecular potential energy surfaces, the masses of the atoms and their coupling, which are specific to every molecule. As a result, the set of wavelengths at which radiation is absorbed by a material (its set of "absorption peaks") is indicative of the chemical makeup of that material. As a result, these absorption peaks are often referred to as "finger-print absorption peaks."

In transmission infrared spectroscopy, infrared radiation is directed through a test sample and detected after it has passed through the material. As the radiation passes through the sample, each chemical constituent of the material selectively absorbs radiation at its characteristic wavelengths, thereby imparting chemistry-dependent spectral information on the detected radiation. The positions, magnitudes, and inflections of the spectral peaks in the output signal provide a "spectral fingerprint" that is then used to estimate the chemical makeup of the sample.

The mid-infrared (MIR) spectral range (defined herein as the wavelengths within the range of approximately 2.5 microns to approximately 12.5 microns) represents a particularly information-rich spectral region because of the wealth of absorption peaks that exist within it for most chemicals. The MIR spectral range, therefore, is an attractive operating range for infrared spectroscopy. As a result, several MIR spectrometers have been disclosed in the prior art, such as those disclosed by Muneeb, et al., in "Demonstration of Silicon on insulator mid-infrared spectrometers operating at 3.8 microns," *Optics Express*, pg. 11659 (2013) and those disclosed by Shankar, et al., in "Silicon photonic devices for mid-infrared applications," *Nanophotonics*, Vol. 3, pg. 329 (2014). Generally, known MIR spectrometers are based on a wavelength dispersion element (e.g., a prism or diffraction grating) that spatially spreads the spectrum of interrogating light across a region of a test sample. The light passes through the test sample and is detected by an array of substantially identical detectors—either semiconductor detectors that measure a photoelectric effect, or bolometers that measure changes in temperature due to absorption of incident radiation. It should be noted that precise alignment between the source, test sample, and detector array is required to enable proper registration between the output signal of each detector and the wavelength of light believed to be incident upon it.

Unfortunately, prior-art MIR spectroscopy systems have many drawbacks. First, conventional MIR spectrometers suffer from narrow bandwidth. Second, their wavelength resolution is too coarse to effectively identify many chemicals—typically due to an insufficient number of detectors. Third, most prior-art MIR spectrometers require external sources and detectors, making them quite complex, difficult to align and keep aligned, and subject to failure due to environmental shock and vibration. Fourth, scatter of radiation within the test sample can lead to cross-talk between detector pixels, since the output signal of each bolometer is merely a function of whatever radiation is incident upon it.

Further, prior-art spectrometers based on semiconductor detectors, which measure photoconductivity or diode current changes, have additional drawbacks. In a semiconductor detector, incident photons excite valence electrons to the conduction band to give rise to a macroscopically detectable electric current. Commonly used mid-IR detectors include mercury cadmium telluride, gallium tin, indium tin, or germanium, each of which has a relatively small electrical bandgap. Because of these small bandgaps, these semiconductors typically have high leakage currents that compromise the signal-to-noise performance of the detectors. To mitigate leakage current, they are normally cooled to below ambient temperature during operation. The need to operate at low temperature, however, severely limits their portability, as well as their use for biological analysis.

While conventional bolometers represent an attractive alternative to semiconductor MIR detectors in many cases, they are not without their own disadvantages. A conventional bolometer detects incident radiation by absorbing the radiation and converting its energy into heat that manifests as a change in temperature. Bolometers typically require materials with large thermo-resistance coefficients, such as vanadium oxide, as well as long light-interaction lengths to enable sufficient absorption for detection. Mid-IR sensitive bolometers observe the conductivity change of thermo-resistive materials deposited onto thermally isolated membranes and can function at room temperature; however, because a bolometer inherently functions as a heat detector, bolometer-based prior-art systems are highly sensitive to changes in ambient temperature.

The need for a practical, high-sensitivity, robust MIR spectrometer remains unmet in the prior art.

SUMMARY OF THE INVENTION

The present invention provides MIR spectroscopy systems that overcome some of the costs and disadvantages of the prior art. Spectrometers in accordance with the present invention employ an MIR radiation signal to interrogate a test sample and a detector array to detect absorption in narrow spectral components of the MIR radiation as it passes through the test sample. The MIR radiation propagates through multiple stages of spectral dispersion in a hierarchical arrangement to spatially separate and direct the spectral components onto individual detector pixels. The spectral dispersion is done in hierarchical fashion with at least one stage on either side of the test sample. In some embodiments, spectral cross-talk is mitigated by using spectrally selective detector pixels, thereby improving system sensitivity. In some embodiments, spectral cross-talk is mitigated by using spectrally selective emitters, each emitting radiation having a spectral sub-range such that all of the spectral sub-ranges collectively span the MIR spectrum.

An illustrative embodiment of the present invention is an MIR hyperspectral spectrometer that includes an array of spectrally selective emitters and an array of spectrally selective detectors, with a hierarchical spectral dispersion system between the emitter and detector arrays. Each emitter in the emitter array selectively provides radiation within a different spectral sub-band of the MIR range such that the emitter array collectively emits radiation across the entire MIR range. The radiation emitted by each emitter is distributed into a plurality of radiation beams by a lens of a first lens array, where each of the plurality of radiation beams includes a spectral sub-band that is a fraction of the spectrum of the radiation received by that lens. The radiation beams are focused onto the lenses of a second lens array located on the opposite side of the test sample such that each radiation signal passes through the test sample and its spectral components are absorbed based on the chemical makeup of test sample. Each lens of the second lens array receives a different radiation beam and distributes it into a plurality of radiation beamlets, each of which is focused on a different detector pixel of a detector associated with that lens. Each radiation beamlet includes a different wavelength component of the radiation beam received by that lens. In addition, each lens of the second lens array receives radiation scattered by the test sample over substantially its entire surface area, where the scatter radiation received by each lens comprises primarily all of the spectral components of the plurality of radiation beams focused on that lens. Each lens is operative for focusing each spectral component in the scatter radiation onto the same detector pixel that receives that same spectral component distributed from the radiation beam received by the lens.

In the illustrative embodiment, each emitter is a miniature black-body radiation source that includes a diffraction grating that gives rise to narrow-spectrum radiation in its spectral sub-range, as well as encouraging the radiation from each emitter to propagate preferentially in a desired direction. In some embodiments, each emitter is optically coupled with an additional diffractive lens that focuses the radiation to give rise to an even more narrow emission pattern. In some embodiments, each emitter includes a mirror layer held above the diffractive elements to define a vertical resonant cavity between them. The inclusion of the mirror layer enables black-body radiation that is more efficiently emitted in the desired narrow spectral sub-range of each emitter.

In the illustrative embodiment, each detector in the detector array includes a group of spectrally selective pixels, each of which detects only one spectral component that includes a narrow sub-portion of the spectral range provided by its corresponding emitter. The detector pixels are cavity-enhanced detector elements defined by photonic crystals formed in a layer of weakly absorbing silicon. The surface structure of the photonic crystal gives rise to excitation of surface states that generates free-carrier pairs in the silicon, thereby enabling the generation of a macroscopically detectable photoconductive response. In addition, the design of each photonic crystal provides spectral selectivity to its respective pixel. In some embodiments, the detector pixels are conventional MIR detectors, such as non-spectrally selective bolometers or MIR-sensitive photoconductors. In some embodiments, a high electric field is applied across each pixel to foster the development of avalanche gain. In some embodiments, at least one pixel group includes a "blind" pixel that enables differential measurement of each "active" pixel referenced to the blind detector. In some embodiments, the pixels are interrogated using a pulsed scheme that enables detection of both its photoconductive and thermal response.

In some embodiments, the pixel group associated with each emitter is optically coupled with a diffractive lens that directs each sub-portion of the spectral sub-range of the radiation provided by that emitter to the appropriate pixel within that group.

In some embodiments, the emitter array and detector array are located on either side of a chamber formed in a microcuvette. The microcuvette includes first and second substrates that are joined to define the chamber. The emitters are formed in a surface of the first substrate, while the detectors are formed in a surface of the second substrate. Joining the substrates automatically aligns each emitter with its associated detector.

In some embodiments, the emitter array is disposed on a first side of a clamping mechanism for holding a test sample, while the detector array is disposed on second side of the clamping mechanism. When the test sample is clamped between the emitter array and detector array, each emitter is aligned with its corresponding detector.

An embodiment of the present invention is a mid-infrared (MIR) spectroscopy system for detecting an analyte in a test sample, the spectroscopy system comprising: 1) a hierarchical spectral dispersion system comprising: (a) a first plurality of lenses arranged to receive a plurality of radiation signals, each having a first spectral range, each lens of the first plurality thereof being operative for receiving a different radiation signal of the plurality thereof and distributing it into a plurality of radiation beams focused at a first focal field, wherein each radiation beam has a second spectral range that is smaller than the first spectral range, and wherein the plurality of second spectral ranges is collectively equal to the first spectral range; and (b) a second plurality of lenses located at the first focal field, each lens of the second plurality thereof being operative for receiving a different radiation beam of the plurality thereof and distributing it into a plurality of radiation beamlets focused at a second focal field, wherein each radiation beamlet has a third spectral range that is smaller than the second spectral range of its respective radiation beam, and wherein the plurality of third spectral ranges is collectively equal to the second spectral range; and a plurality of detector pixels located at the second focal field, the plurality of detector pixels being arranged such that each detector pixel receives a different radiation beamlet of the plurality thereof; wherein the plurality of first spectral ranges collectively spans the MIR spectrum.

Another embodiment of the present invention is a hyperspectral spectroscopy system comprising: a hierarchical spectral dispersion system that is dimensioned and arranged to distribute the spectral components of a first plurality of radiation signals into a plurality of radiation beamlets, the first plurality of radiation signals collectively spanning a first spectral range that is at least a portion of the mid-infrared (MIR) spectrum, and each radiation beamlet including a different spectral component included in the first spectral range such that the plurality of spectral components collectively spans the first spectral range, each spectral component having a second spectral range that is smaller than the first spectral range; and a plurality of detectors, each detector including a plurality of detector pixels, and each detector pixel being spectrally selective such that it detects only one spectral component of the plurality thereof; wherein the hierarchical spectral dispersion system and the plurality of detectors are arranged such that each radiation beamlet of the plurality thereof is directed to the detector pixel that is spectrally selective for its respective spectral component.

Yet another embodiment of the present invention is a method for analyzing a test sample, the method comprising: distributing each of a first plurality of radiation signals into a first plurality of radiation beams, each radiation signal being characterized by a different first spectral range such that the plurality of first spectral ranges collectively spans at least a portion of the MIR spectrum; focusing each radiation beam of the first plurality thereof at a first focal field such that the first plurality of radiation beams interacts with the test sample to give rise to a second plurality of radiation beams whose spectral content is based on the chemical composition of the test sample, wherein each radiation beam of the second plurality thereof has a different second spectral range that is smaller than the first spectral range of its respective radiation signal, and wherein each plurality of second spectral ranges collectively spans the first spectral range of its respective radiation signal; distributing each radiation beam of the second plurality thereof into a plurality of radiation beamlets that are focused at a second focal field, each radiation beamlet having a spectral component characterized by a different third spectral range that is smaller than the second spectral range of its respective radiation beam of the second plurality thereof, and wherein each plurality of third spectral ranges collectively spans the second spectral range of its respective radiation beam of the second plurality thereof; detecting the plurality of radiation beamlets at a plurality of detectors located at the second focal field, wherein each detector provides an output signal based on respective radiation beamlet; and detecting at least one analyte in the test sample based on the plurality of output signals.

BRIEF DESCRIPTION OF THE DRAWINGS

FIGS. 6A-B depict schematic drawings of cross-sectional and perspective views, respectively, of a first spectrometer arrangement in accordance with the present invention.

FIG. 10 depicts a schematic drawing of a cross-sectional view of a third spectrometer arrangement in accordance with the present invention.

DETAILED DESCRIPTION

In is an aspect of the present invention that significant advantages over MIR spectroscopy systems of the prior art are derived by employing a hierarchical wavelength-segmentation approach. In embodiments of the present invention, the MIR spectrum is segmented into a plurality of spectral sub-ranges by employing an array of emitters, each of which emits radiation in only one of the spectral sub-ranges. The radiation from each emitter is further segmented by directing it only onto a detector comprising a plurality of detector pixels, each of which selectively detects radiation in a sub-portion of the spectral sub-range of that detector. Further, each detector is optically coupled with its respective emitter via a filter element that directs each sub-portion to its corresponding detector pixel. The use of multiple emitters in an array, along with diffractive optical filters that match those sources with spectrally selective detector elements, the entire MIR spectrum can be detected with finer spectral resolution and less spectral cross-talk than can be achieved in the prior art.

For the purposes of this Specification, including the appended claims, "spectrally selective" is defined as having greater responsivity within a specific range of wavelengths for which a device is designed to be operative. For example, a spectrally selective emitter emits radiation having greater intensity within a spectral range defined by its full-width at half maximum. In similar fashion, a spectrally selective detector detects only radiation whose wavelengths are within a defined range of wavelengths and is substantially non-responsive for radiation wavelengths outside of that defined range of wavelengths.

In order to provide a fundamental understanding of the inventive aspects of the present invention, an overview of a representative spectroscopy system and its operation is provided here.

Principle of the Invention and Generalized Structure

Figure 1:
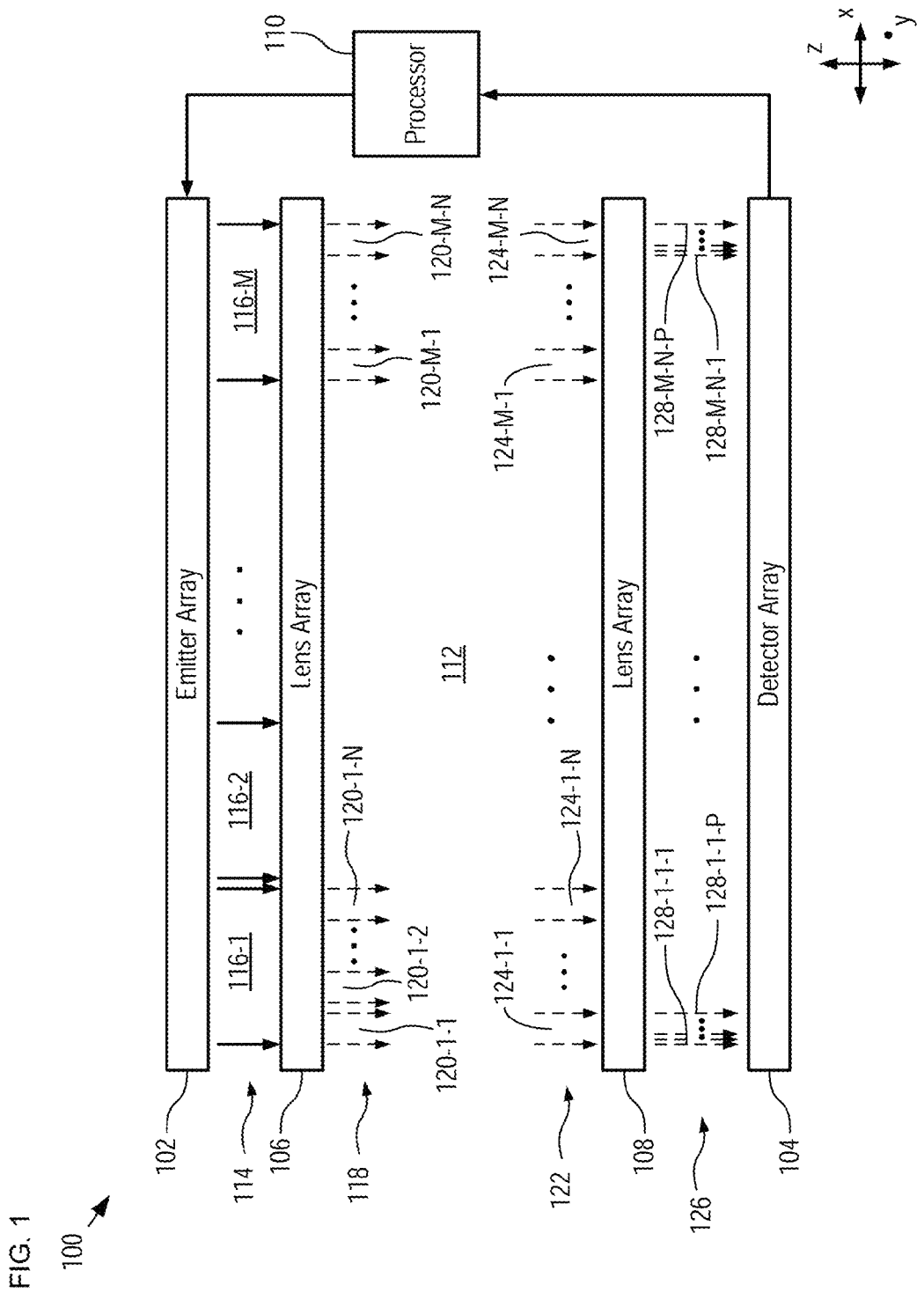
FIG. 1 depicts a schematic drawing of the salient features of a representative spectroscopy system, and their functional relationship, in accordance with the present invention.

FIG. 1 depicts a schematic drawing of the salient features of a representative spectroscopy system, and their functional relationship, in accordance with the present invention. System 100 is a hyperspectral spectroscopy system that analyzes a test sample using mid-infrared radiation. System 100 is suitable for interrogating test samples comprising myriad materials including, without limitation, bodily fluids (e.g., blood, spittle, etc.), biological tissue, industrial fluids, petroleum products, and the like. System 100 includes emitter array 102, detector array 104, lens arrays 106 and 108, and processor 110.

Emitter array 102 is an array of M black-body-radiation emitters that collectively provide radiation 114. As discussed below, each emitter in emitter array 102 is spectrally selective such that it provides a radiation signal that is substantially concentrated within a narrow sub-range of wavelengths within the MIR spectrum. In emitter array 102, each emitter is dimensioned and arranged such that emits a radiation signal 116 whose energy is concentrated in a different spectral sub-range of the MIR spectrum such that radiation 114 spans the entire MIR spectral range. Emitter array 102 is described in more detail below and with respect to FIGS. 2A-B.

Detector array 104 is an array of spectrally selective detectors, each of which is dimensioned and arranged to detect radiation having wavelengths only within a narrow band of wavelengths within the MIR spectrum. Each detector of detector array 104 is designed such that its response is substantially matched to the spectral sub-range of the radiation emitted by the emitters of emitter array 102 with which it is aligned. In other words, each detector of detector array 104 is designed to detect radiation only within a different one of the spectral sub-ranges of radiation signals 116-1 through 116-M. Detector array 104, therefore, collectively detects radiation having wavelengths that span the entire MIR spectral range.

As discussed below, each detector in detector array 104 includes a plurality of detector pixels, each of which is designed to selectively detect a spectral component that is a small fraction of the spectral range received by that detector as a whole. Typically, the ratio of detector pixels to emitters is within the range of 10 to approximately 300 and the wavelength selectivity of each pixel is a spectral width within the range of approximately 0.5 nm to 10 nm. Detector array 104 is described in more detail below and with respect to FIGS. 3A-D.

Emitter array 102 and detector array 104 are arranged on either side of test sample 112 such that detector array 104 receives radiation 122, which is based on radiation 114 after it has passed through the test sample. Lens arrays 106 and 108 are located between the emitter array and detector array to spatially distribute, in hierarchical fashion, the spectral components within the spectral sub-range of each radiation signal 116 and direct each spectral component onto its corresponding detector pixel.

Lens array 106 is an array of M diffractive lenses arranged to receive radiation 114 from emitter array 102 such that each lens in lens array 106 receives a different radiation signal 116. Lens array 106 includes N diffractive lenses, each of which spatially distributes its received radiation signal into a plurality of radiation beams 120, each which includes a different spectral sub-portion of the spectral sub-range of the radiation signal it receives. Lens array 106 focuses each of radiation beams 120 as a spot at a different lens in lens array 108. As a result, for each radiation signal 116-$i$, where i=1 through M, radiation beams 1204-1 through 120-$i$-N collectively span the spectral sub-range of that radiation signal. Lens array 106 directs radiation beams 120-1-1 through 120-M-N (referred to, collectively, as radiation beams 120) through test sample 112 such that the test sample is interrogated by the entirety of the MIR spectrum. Lens array 106 is described in more detail below and with respect to FIG. 5A.

As discussed above, as radiation 118 passes through test sample 112, certain wavelengths in the radiation are absorbed based on the chemical makeup of the test sample. As a result, the transit of each of radiation beams 120 through test sample 112 imprints the absorption characteristics of the test sample material on its respective spectral sub-portion, giving rise to radiation beams 124-1 through 124-M (referred to, collectively, as radiation beams 124), which collectively define radiation 122.

Emitter array 102, detector array 104, and lens arrays 106 and 108 are aligned such that the emitters and detectors that are spectrally selective for the same spectral sub-ranges are optically coupled. As a result, each detector provides an output signal to processor 110 that is indicative of the absorption that occurs only within one specific spectral sub-range.

Lens array 108 is an array of M diffractive lenses that receives radiation signal 122 and provides radiation 126 to detector array 104. Each lens in lens array 108 includes N lenslets. As a result, lens array 108 collectively includes M*N lenslets. Each lenslet in lens array 108 is operative for receiving a different radiation beams 124, spatially partitioning it, by wavelength, into P radiation beamlets 128, each containing a different, narrow-width spectral component, and distributing the radiation beamlets to the appropriate detector pixels of its respective detector. For example, for i=1 through M and 1=1 through N, radiation beam 124-$i$-$j$ is partitioned into radiation beamlets 128-$i$-$j$-1 through 128-$i$-$j$-P. Lens array 108 is described in more detail below and with respect to FIGS. 3A-D and 5B.

Processor 110 is a conventional computer processor operative for controlling the emitters of emitter array 102 and performing analysis of the output signals provided by detector array 104.

It should be noted that, although system 100 preferably operates in transmission mode, as shown, in some embodiments, system 100 is arranged to operate in reflection mode, wherein emitter array 102 and detector array 104 are located on the same side of test sample 112 and radiation 122 is a portion of radiation 118 that is reflected substantially from the surface of the material of test sample 112.

It should be noted that, in embodiments that operate in reflection mode, the radiation reflects from the sample in an approximately hemispherical dispersion that includes all wavelength components in the MIR spectrum. As a result, it is necessary to account for the substantially uniform distribution of the wavelength components in the reflected radiation. For a full spectrum radiation (all filaments illuminated at the same time) from emitters the reflected radiation would be presented to the diffractive lens that accept the 10-12.5 um detector bandwidths would pass some harmonics from the 5-10 um illuminations, and would also pass some of the higher harmonics from the 2.5-5 um illuminations. Similarly, the reflected radiation presented to the diffractive lens that accept the 5-10 um detector bandwidths and would pass some harmonics from 2.5-5 um illuminations. In some embodiments, this is problem is resolved by time multiplexing the emitter filaments that emit in these three broad radiation bandwidths. While the diffractive lenses in lens array 108 designed for each harmonic would receive radiation in each of the other harmonics, the time-multiplexed nature of the illumination enables reconstruction of the spectral profile of the test sample because it enables determination of the harmonic in which the detected wavelengths reside.

Figure 2A:
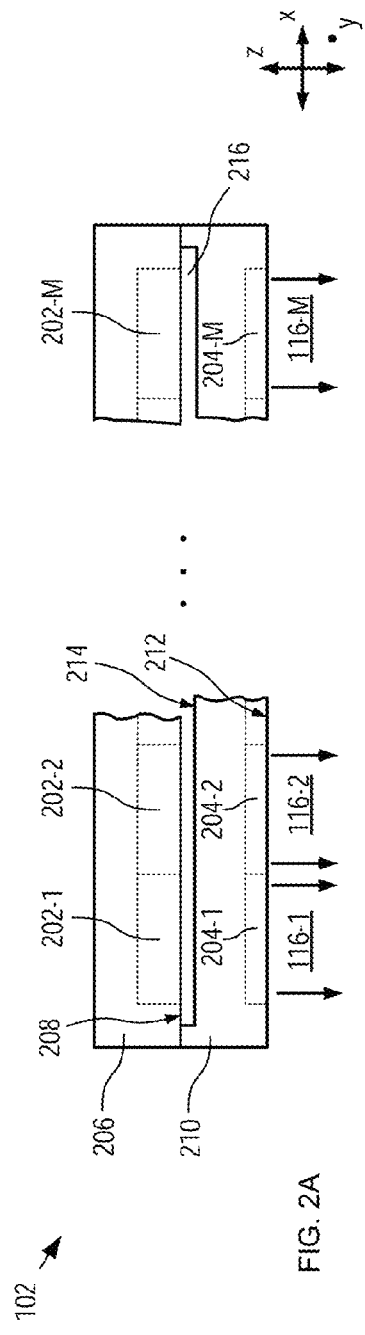
FIG. 2A depicts a schematic drawing of a side view of emitter array 102.

FIG. 2A depicts a schematic drawing of a side view of emitter array 102. Emitter array 102 includes emitters 202-1 through 202-M and lenses 204-1 through 204-M. It should be noted that the use of at least three groups of emitters 202, each of which emits wavelengths of a different harmonic, mitigates the propagation of wavelength harmonics through system 100. The wavelengths within the range of 2.5 microns to 5 microns constitute a first harmonic, wavelengths within the range of 5 microns to 10 microns constitute a second harmonic and wavelengths within the range of 10 microns to 12.5 microns constitute a portion of a third harmonic.

Emitters 202-1 through 202-M (referred to, collectively, as emitters 202) are formed at surface 208 of substrate 206.

It is an aspect of the present invention that the emission spectrum, as well as the direction of emission, of radiation emitted by a black-body source can be tailored by designing the source based on diffractive-optics and antenna-array principles. In contrast to a conventional black-body emitter, which generates a spectrum that follows Planck's relationship and is largely controlled by the emitter temperature, the radiation generated by emitters in accordance with the present invention can be preferentially emitted into desired directions by using an appropriate shape for individual emitting elements and spacing them properly.

Figure 2B:
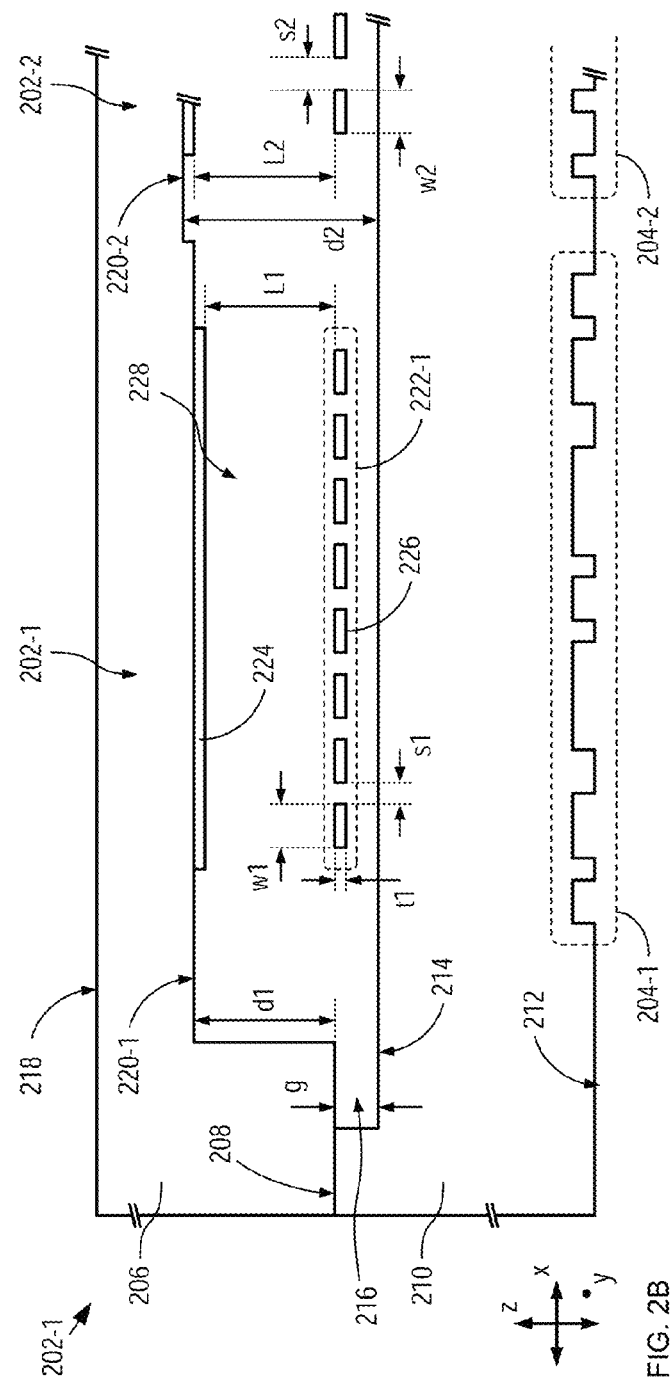
FIG. 2B depicts a schematic drawing of a cross-section of a portion of emitter array 102.

FIG. 2B depicts a schematic drawing of a cross-section of a portion of emitter array 102. FIG. 2B provides an enlarged view of individual emitter 202-1 and its associated lens 204-1. Emitter 202-1 is representative of each of emitters 202-1 through 202-M; however, the dimensions of the elements that compose each emitter are specific to the spectral sub-range 116 of that emitter. Each emitter 202 comprises filament 222 and mirror 224.

Figure 2C:
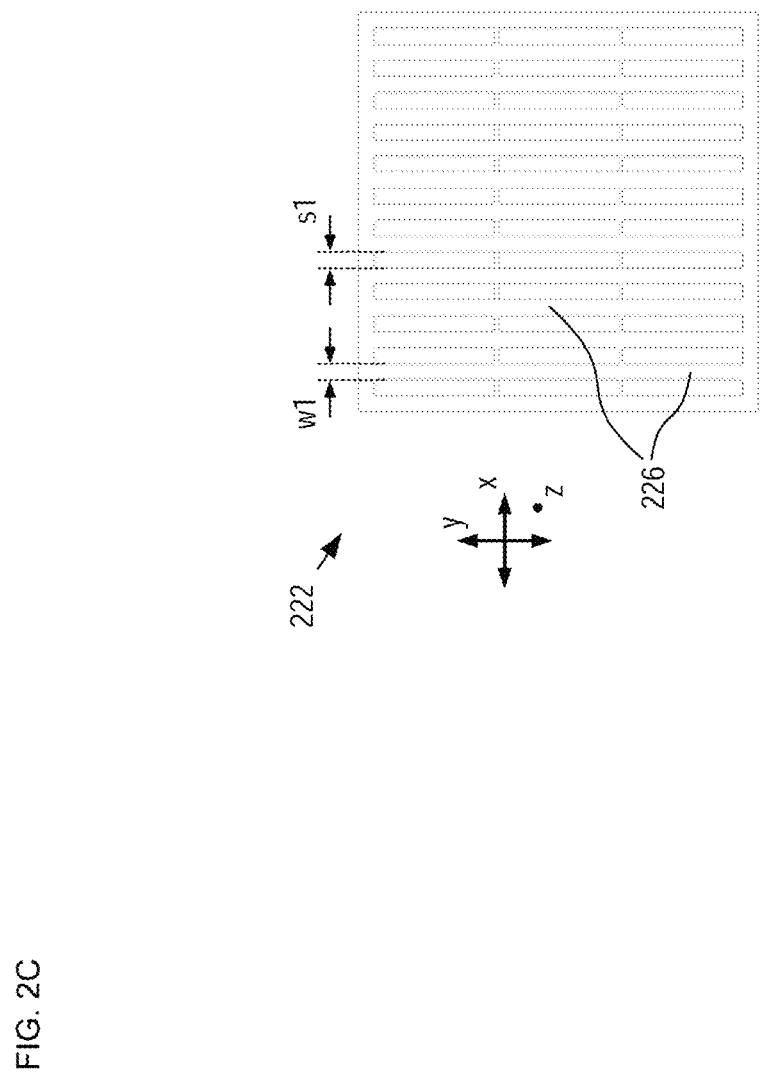
FIG. 2C depicts a schematic drawing of a top view of a representative filament 222.

FIG. 2C depicts a schematic drawing of a top view of a representative filament 222.

Emitter array 102 is typically formed via conventional MEMS-based fabrication process. In the depicted example, fabrication of the emitter array begins with the formation of through-wafer interconnects (not shown for clarity) that enable electrical connectivity between surfaces 208 and 218 of substrate 206. Typically, contact pads in electrical communication with the through-wafer interconnects are also formed on surface 218 (not shown for clarity).

Substrate 206 is a substrate suitable for conventional planar processing and, preferably, comprises float-zone silicon; however, any practical substrate material can be used for substrate 206 (e.g., ceramics, compound semiconductors, etc.). It is an aspect of the present invention that the use of float-zone silicon for at least substrate 210 affords significant advantages over the prior art. First, it is substantially transparent out into the far-infrared spectral range due to its extremely low doping levels. Second, silicon is inexpensive and fabrication of silicon devices is well understood. Third, its high refractive index and transparency for MIR wavelengths makes it possible to sculpt diffractive-optics elements for filtering and focusing radiation. Fourth, it is absorptive for visible and near-infrared radiation, which enables the use of the substrate for blocking undesired radiation from entering spectroscopy system 100.

Surfaces 220-1 through 220-M (referred to, collectively, as surfaces 220 are then formed by etching surface 208 to a different depth at the location of each emitter 202 to form surfaces 220-1 through 220-M. For example, surface 208 is etched to a depth of d1 to form surface 220-1 at the site of emitter 202-1, d2 to form surface 220-2 at the site of emitter 202-2, and so on, where each etch depth is substantially equal to one-half the center wavelength of the spectral sub-range 116 of that emitter. As discussed below, the depth of surface 220 at each emitter dictates the cavity length, L, of a resonant cavity defined by mirror 224 and filament 222.

Mirrors 224 are then formed on each of surfaces 220 by conventional deposition and patterning techniques. Each of mirrors 224 is a region of a refractory metal (e.g., tungsten, platinum, etc.) having an area that is typically slightly larger than the extent of filament 222.

A layer of sacrificial material, such as a polymer, is then formed in the etched region of surface 208 to planarize substrate 206.

Emitting elements 226 are then formed on the sacrificial layer via conventional deposition and patterning to collectively define filament 222. Emitting elements 226 comprise lines of refractory metal having thickness, t, emitter width, w, and emitter spacing, s, which collectively define an MIR antenna array/diffraction grating. One skilled in the art will recognize, after reading this Specification, that the values of t, w, and s dictate the emission spectrum and directionality of radiation emitted by an emitter. For example, the emitting elements of emitter 202-1 have emitter thickness t1, emitter width w1 and are separated by emitter spacing s1, which collectively define a diffraction grating that encourages emission within a first desired spectral sub-range and along the z-direction, as indicated. In similar fashion, the emitting elements of emitter 202-2 have thickness t2 emitter width w2 and are separated by emitter spacing s2, which collectively define a diffraction grating that encourages emission within a second desired spectral sub-range and along the z-direction.

For an exemplary emitter array wherein M=10, each of emitters 202 emits a radiation signal 116 having wavelengths only within a spectral sub-range whose spectral width is approximately one micron. In such an emitter array, therefore, emitter 202-1 preferentially emits sub-range 116-1 having wavelengths that span the range of 2.5 microns to 3.5 microns, emitter 202-2 preferentially emits sub-range 116-2 having wavelengths that span the range of 3.5 microns to 4.5 microns, and so on, with emitter 202-10 preferentially emitting sub-range 116-10 having wavelengths that span the range of 11.5 microns to 12.5 microns. It should be emphasized that, in practice, M can be any practical number and emitters 202 can have emit over any spectral sub-ranges commensurate with the value of M.

After formation of filaments 222, the sacrificial layer between mirrors 224 and emitting elements 226 is removed. It should be noted that the removal of the sacrificial layer also substantially thermally decouples filaments 222 from substrate 206, thereby reducing the thermal load that must be driven to emit radiation.

Each filament 222 and its associated mirror 224 collectively define a vertical resonant cavity 228, which establishes a resonance between black-body emissions directed toward the mirror by the heated filament. For each of emitters 202, its resonant cavity 228 has cavity length L, which is equal to one-half of the center wavelength of its respective sub-range 116. This resonance enables preferred radiation filtration and photon recycling of those black-body emitted photons that would otherwise be lost into substrate 206. By virtue of the spaces between emitting elements 226, the filament is substantially semitransparent, which makes resonant cavity 228 highly efficient and operative for changing the black-body-emission rate. The design of filament 222 and resonant cavity 228 enable emission from each emitter that is enhanced within the spectral sub-range of its specific radiation signal 116 at the expense of energy at wavelengths outside that sub-range. By "stealing" energy from the higher and lower frequency ranges, in addition to enhancing emission in the desired spectral band (i.e., in-band radiation), the intensity in the higher and lower ranges (i.e., out-of-band radiation) is also reduced. It should be noted that the in-band radiative flux of a diffraction grating system can be greater than the equivalent band blackbody flux from the surface of the sun—a temperature much greater than the melting point of the refractory metal filament. It should also be noted that emitters 202 provide in-band emissions that are substantially insensitive to the temperature of the filament itself.

One skilled in the art will recognize that radiation from a black-body emitter is typically emitted into all directions. As discussed above, the diffraction grating structure of filaments 226 and resonant cavity 228 give rise to radiation propagation more generally along the z-direction, however. Even with these structural elements, additional beam shaping, such as collimating or focusing, of the emitted radiation is typically desirable. As a result, emitter array 102 optionally includes diffractive optical elements for shaping the radiation emitted by emitters 202.

The fabrication of substrate 210 begins with the formation of lenses 204-1 through 204-M (referred to, collectively, as lenses 204) surface 212 of the substrate. Substrate 210 is analogous to substrate 206. Each of lenses 204 is a conventional diffractive lens (e.g., Fresnel lens, binary-phase grating, holographic element, etc.) that is designed to focus a different spectral sub-range of radiation emitted by emitters 202 onto a different lens of lens array 108. In some embodiments, lenses 204 are collimating lenses.

Cavity 216 is then formed in surface 214 of substrate 210.

Substrates 206 and 210 are then aligned and joined to locate cavity 216 emitters 202 such that the emitters are substantially thermally isolated from substrate 210. In addition, lenses 204 are aligned with emitters 202 such that each lens receives the proper radiation from its respective emitter and directs it onto a corresponding detector of detector array 104.

It should be noted that the fabrication process outlined above is merely exemplary and that myriad alternative processes can be used to form emitter array 102 without departing from the scope of the present invention.

Figure 3A:
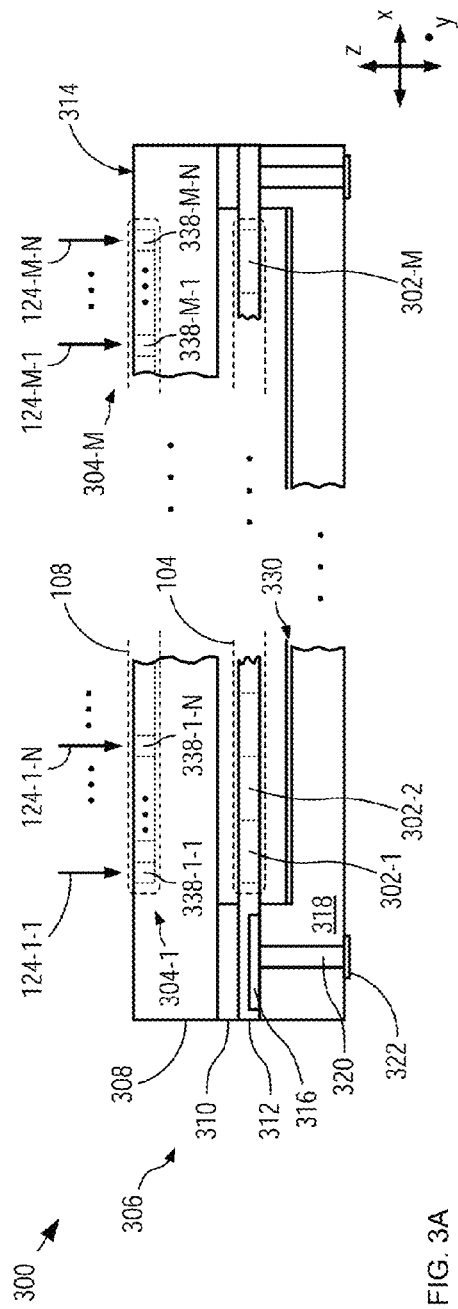
FIGS. 3A-B depict schematic drawings of a cross-sectional view of a detector module and a cross-sectional view of a representative individual detector/lens pair (specifically, detector 302-1/lens 304-1), respectively, in accordance with the present invention.
Figure 3B:
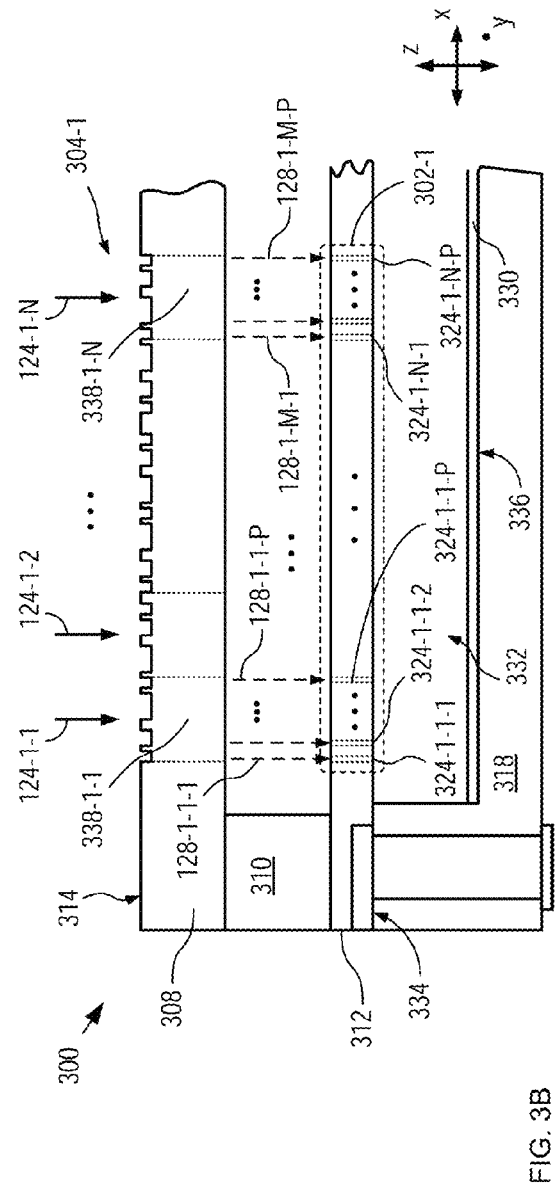

FIGS. 3A-B depict schematic drawings of a cross-sectional view of a detector module and a cross-sectional view of a representative individual detector/lens pair (specifically, detector 302-1/lens 304-1), respectively, in accordance with the present invention. Detector module 300 includes detector array 104 and lens array 108. Detector array 104 includes detectors 302-1 through 302-M. Lens array 108 includes lenses 304-1 through 304-M. Like emitter array 102, detector array 104 is typically fabricated using conventional MEMS-based fabrication processes. In some embodiments, detector array 104 and lens array 108 are separate components.

Detectors 302-1 through 302-M (referred to, collectively, as detectors 302) are formed in active layer 312 of substrate 306, which is silicon-on-insulator (SOI) substrate comprising handle substrate 308, buried oxide (BOX) layer 310, and active layer 312. Each of handle substrate 308 and active layer 312 is made of float-zone silicon. Typically the structure of detectors 302 is defined in the active layer via conventional photolithography and deep reactive-ion etching (DRIE). Preferably, BOX layer 310 has a thickness that is equal to or greater than 5 microns and active layer 312 has a thickness that is at least 3 microns. In some embodiments, an organic layer is used in place of BOX layer 310. This approach enables the replacement of the active layer, which is presently envisioned to be active silicon, but alternative materials that can be "glued" onto the polymer layer. In some embodiments, active layer 312 comprises a material other than silicon. Materials suitable for use in active layer 312 include, without limitation, gallium arsenide, diamond, zinc selenide, and multi-layer semiconductor layer stacks.

Electronics module 316 is also formed in active layer 312 in conventional fashion. Electronics module 316 typically includes electronics for managing the output signals from each of detectors 302, providing signal amplification, and frequency filtering, among other functions.

In the regions of detectors 302, BOX layer 310 is removed so that this region of active layer 312 is physically separated and substantially thermally isolated from handle substrate 308. It should be noted that the removal of BOX layer 310 also mitigates evanescent coupling of radiation between detectors 302 and handle substrate 308.

Lens array 108 is formed in surface 314 of handle substrate 308 such that lenses 304-1 through 304-M are aligned with their corresponding detectors 302-1 through 304-M.

Cap substrate 318 is a substrate comprising float-zone silicon that includes through-wafer interconnects 320 and bond pads 322. Cap substrate 318 also includes absorbing surface 330 at surface 336 of cavity 332 to mitigate noise due to backscattered radiation from this surface. Cavity 332 is formed by etching back surface 334 in conventional fashion. Absorbing surface 330 is a layer of absorbing material (e.g., a polymer, etc.) deposited on surface 336. In some embodiments, the absorbing surface is a "moth-eye" structure formed by etching surface 336.

Once fully formed, cap substrate 318 and SOI substrate 306 are bonded to mechanically join them, as well as establish electrical connectivity between through-wafer interconnects 320 (and contact pads 322) and electronics module 316 and detectors 302.

Once the two substrates are bonded, the detectors are fully surrounded by float-zone silicon, which affords embodiments of the present invention with particular advantage. In such a structure, the silicon substrates both filter out unwanted stray radiation by, for example, absorbing wavelengths in the visible and near-infrared spectra. Further and concentrate radiation of different wavelengths into the silicon detectors, thereby shielding the detectors in active layer 312. Further, the use of double-side polished silicon substrates facilitates the formation of lens array 106 on the back side (i.e., surface 314) of substrate 308 to filter different frequencies of radiation and direct them to specific detector pixels, as discussed below.

Although any bonding process (e.g., electrostatic bonding, wafer bonding, low temperature glass bonding, diffusion bonding, eutectic alloy bonding, plasma-assisted bonding, etc.) can be used to join two substrates (e.g., substrates 308 and 318 or substrates 206 and 210) in accordance with the present invention, in some embodiments, it is preferable that substrate bonding be performed using a solid-liquid diffusion (SLID) bonding. SLID bonding is a variation of eutectic bonding, which is widely used throughout the MEMS industry.

In conventional eutectic bonding, thin foils of low-melting-point metal (e.g., gold alloys) are deposited in bond regions on the separate substrates. The bond regions are then held in close contact with each other, usually under pressure. The substrate pair is then heated and solid state diffusion occurs forming a bond between the two bond regions at a temperature below the melting point of the eutectic alloy (diffusion bonding). In order to minimize the bonding temperature, the correct weight percentage of each compound must be used. The proper weights are typically determined from the eutectic point chosen from a binary phase diagram for the material.

In SLID bonding, the eutectic metal in the bond regions is allowed to melt and liquid-phase bonding between the two regions occurs. Since diffusion in the liquid state is about three times faster than in the solid state, the regions are joined more rapidly and less pressure is necessary. If the ratio of the materials in the bonding regions is adjusted such that the mixture has a melting point above the eutectic temperature, then upon reaching the eutectic temperature, melting at the interface begins. More material is consumed by the melt as long as the eutectic composition can be maintained. As one of the components becomes depleted, the liquidus point increases and the mixture partially solidifies. In thermal equilibrium, the Lever law can be used to determine the ratio of compounds in the liquid and solid state.

In some embodiments of the present invention, gold-alloy-based SLID bonding is used to provide electrical and thermal conductivity bonds, as well as hermetic sealing, constant inner die separation and zero-creep fusion. In some embodiments, such as some embodiments that include VLSI electronic circuits, a lower melting point bonding material is used (e.g., indium alloys, etc.).

In the depicted example, zero-thickness SLID-based bonding is used to join substrates 308 and 318.

Figure 4A:
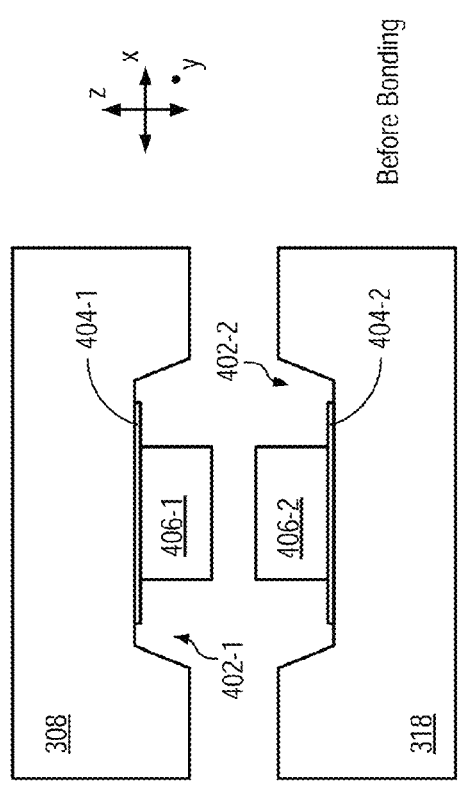
FIGS. 4A-B depict schematic drawings of cross-sectional views of a zero-thickness bond before and after bonding, respectively.
Figure 4B:
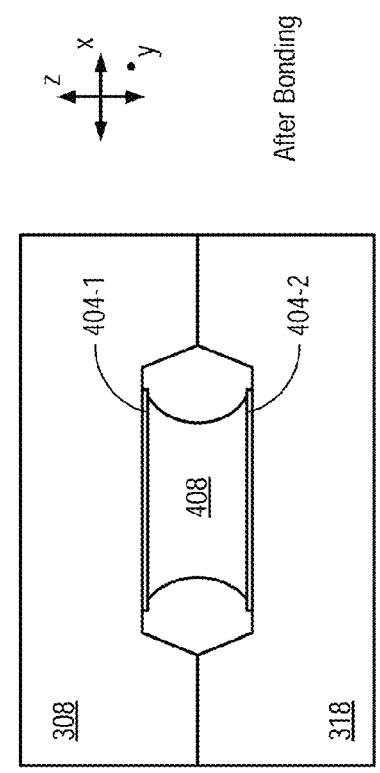

FIGS. 4A-B depict schematic drawings of cross-sectional views of a zero-thickness bond before and after bonding, respectively.

In bond 400, channels 402-1 and 402-2 are formed in each of substrates 308 and 318, respectively. Spreading layers 404-1 and 404-2 are then formed on the bottom of each channel. Spreading layers 404 comprise a material that wets the material of bumps 406-1 and 406-2, which are formed on the spreading layers such that they are smaller than the spreading layers and project slightly above the surface of each of the substrates as shown.

To initiate the bond, bumps 406-1 and 406-2 are brought into contact and the substrates are heated. Upon heating, the bond metal in the bumps melts to form common bump 408 and spreads over spreading layers 404-1 and 404-2, which reduces the spacing between the substrates to zero. This wicking and capillary attraction increases the surface-contact pressure of the bonded substrates. As the substrates cool down after bonding, the surface-contact pressure is increased further by differential shrinkage, which gives rise to tension in the bond metal that ensures that the respective wafer surfaces remain compressed together throughout the aggregate of mechanical forces, pressure loadings, vibrational loadings or thermal excursions imparted on detector module 300.

Returning now to detector module 300 and FIGS. 3A-B, detector 302-1 includes detector pixels 324-1-1-1 through 324-1-N-P, each of which is a high-Q cavity-enhanced silicon detector having responsivity tuned to a different sub-portion of the spectral sub-band of radiation beam 124-1. As a result, each detector 302 in detector array 104 includes N*P detector pixels and detector array 104, therefore, collectively includes M*N*P detector pixels. Detector 302-1 is representative of each of detectors 302; however, one skilled in the art will recognize that the design of each detector is based on the specific spectral sub-band of the radiation signal it receives.

Figure 3C:
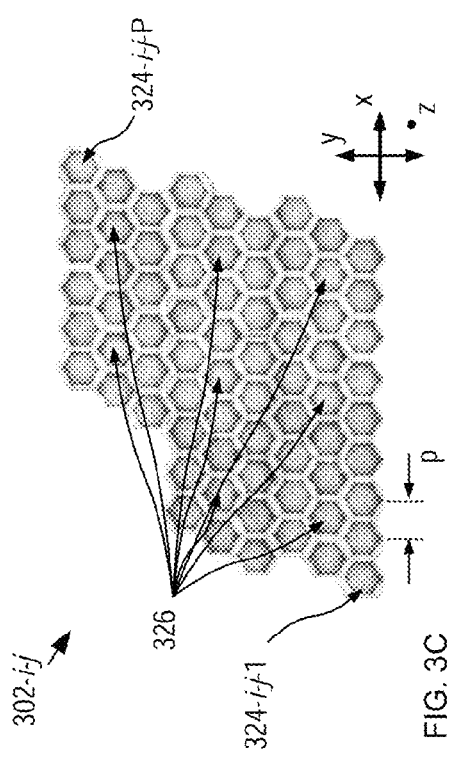
FIG. 3C depicts a schematic drawing of a top view of the pixel arrangement of a representative detector.

FIG. 3C depicts a schematic drawing of a top view of the pixel arrangement of a representative detector. Detector 302-$i$ includes pixels 3244-1-1 through 324-$i$-N-P (referred to, collectively, as pixels 324), where i is an integer within the range of 1 through M. Pixels 324 are arranged in a hexagonal close-packed arrangement having pitch, p, along the x-direction. The magnitude of p is based on the range of wavelengths in the radiation beam 124 received at that detector and ranges from approximately 15 microns for radiation beam 124-1 to approximately 75 microns for radiation beam 124-M. It should be noted that the number of detector pixels normally included in each detector 302 is within the range of approximately 10 to 5000; however, a detector can include any practical number of pixels. Further, pixels 324 can be arranged in any suitable one- or two-dimensional arrangement within a detector region. It should be noted that, typically, each of pixels 324 has an area that is larger than the area of the radiation beamlet 128 that is focused upon it to provide a larger collection area for particular pixel and to provide some alignment tolerance between the emitter, lens, and detector arrays.

It should be noted that, in accordance with the present invention, the size of each pixel is based on the wavelength of radiation to which it is sensitive. For example, the pixels of detector 302-1 are much smaller (approximately 15 microns in diameter) than the pixels of detector 302-M (approximately 75 microns in diameter). By scaling pixel size based on wavelength, the present invention enables detector sensitivity to be substantially normalized.

It is an aspect of the present invention that, in contrast to widely held expectations, silicon can be used to form a photoconductive radiation detector that is sensitive in the MIR spectrum. Silicon has been widely used as a detector material in the visible spectrum, enabling active CMOS and CCD cameras. It has not been used widely as a detector for radiation in the MIR spectrum, however, because it is widely believed that silicon does not absorb radiation with energies below its bandgap of 1.1 eV, which equates to radiation having wavelengths equal to or greater than 1.06 microns.

In fact, embodiments of the present invention exploit both the transparency as well as the manufacturability of silicon to realize narrow-band spectrally selective photoconductive detector arrays that enable hyperspectral MIR spectrometer performance that exceeds the capabilities of prior-art MIR spectrometers. In the mid-IR spectrum, silicon is highly transparent and radiation absorption is limited by defects in the silicon lattice, such as impurities, vacancies and surface states. If silicon is patterned, therefore, surface states are created that turn silicon into a useful photoconductive material for radiation in the near-infrared and mid-infrared wavelength regions.

It is an aspect of the present invention that the amount of absorption in silicon can be controlled by the microfabrication process and the geometry chosen during the detector pixel fabrication. Detector pixels in accordance with the present invention are defined in float-zone silicon, which is normally a weak absorber for radiation in the MIR spectrum. By forming surface features in the silicon having lateral dimensions within the range of 20-50 microns, depending on the wavelength to be detected, tens to thousands of detector pixels can be integrated into an array, where each detector pixel is sensitive to only a specific narrow spectrum, which is determined by the precise detector geometry. Although MIR radiation is not efficiently absorbed in the silicon, photoconductive response is observed from the excitation of surface states on the sculpted surfaces of each pixel. The sensitivity of each pixel to specific wavelengths and the number of surface states can be modified through geometric changes and surface modification, which enable the tuning of the sensitivity of individual detector pixels.

It is another aspect of the present invention that the inclusion of one or more "blind" pixels in each detector enables differential measurement of pixel response wherein background noise due to optical and electronic interference is removed. For example, detector 302-$i$ includes a blind pixel 326 in the center of each 3×3 cluster of pixels. For the purposes of this Specification, including the appended claims, a "blind pixel" is defined as a pixel having a resonant cavity whose resonance is outside the spectral range of the radiation for which its detector is sensitive and is, therefore, substantially insensitive for such radiation. By subtracting the photocurrent of the blind cavity from that of the optimized cavities (having very similar geometries and thermal mass), noise is significantly reduced and the sensitivity of the detector pixels is improved by a factor of approximately 100.

Figure 3D:
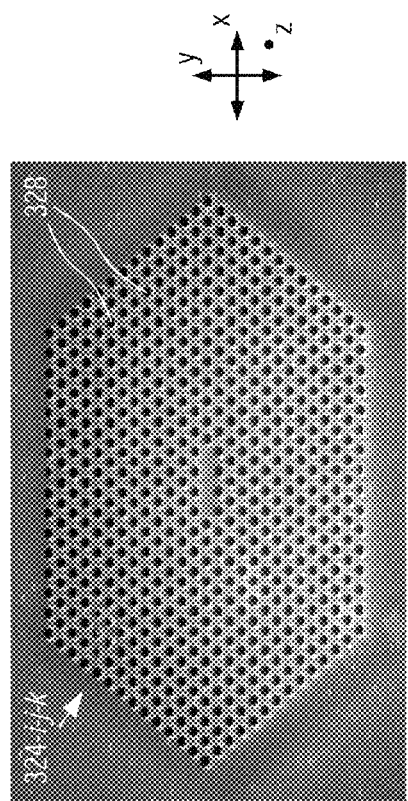
FIG. 3D depicts a schematic drawing of a top view of a representative detector pixel.

FIG. 3D depicts a schematic drawing of a top view of a representative detector pixel. Pixel 324-$i$-$j$-$k$, where k=1 through P, includes a hexagonal arrangement of through-holes 328 that define a photonic crystal, which is a planar high-Q resonator cavity that provides the pixel with wavelength-sensitivity having a narrow-band spectral response. Pixel 324-$i$-$j$-$k$ can be designed for high finesse in silicon, which is substantially a transparent material, thereby reducing the spectral window of the pixel response, $\Delta\lambda$, to $\Delta\lambda/Q$, which can approach approximately $\lambda/20,000$ for planar high-Q cavities in silicon. Here, $\lambda$ is the wavelength of the radiation to be detected and Q is the quality factor of the resonator cavity.

It should be noted that, as radiation is absorbed more efficiently within a material, the cavity Q is reduced, which broadens the spectral width of the detection window $\Delta\lambda/Q$. For conventional MIR-absorbing materials, for example, the optimum Q is reduced from 20,000 to 100, resulting in a deterioration of the spectral linewidth at ~10 micron wavelength from approximately 1 nm to 100 nm. A pixel detection window of order 100 nm would be unacceptable for many applications of MIR biochemical spectroscopy. In contrast to the prior art, however, the use of weakly absorbing silicon for the material of pixels 324 enables pixel detection windows of approximately 2-nm width. Further, the specific geometry of each pixel determines its cavity resonance wavelength giving rise to sensitivity to only radiation that matches that wavelength.

As a result, embodiments of the present invention derive several advantages as a result of employing in-plane optical cavities formed entirely by microfabrication of photonic crystal cavities. First, the propagation of incident radiation is translated from out-of-plane (in the z-direction) to in-plane (in the x-y plane), which increases the path length of the radiation within the optical cavity thereby increasing the efficiency of the optical field overlap between active absorbing material and the incident radiation. This gives rise to improved sensitivity of the detector pixel. Second, the spectral selectivity of the detector is improved, as noted above, resulting in 2 nm spectral resolution. Third, light not within the wavelength range for which the photonic crystal is sensitive does not translate from out-of-plane to in-plane radiation and, instead, passes straight through the device. As a result, the interaction length in the silicon material for such wavelengths is very short limiting its absorption to minimal levels.

It should be noted that the photonic-crystal cavities used to filter specific wavelengths into individual detector pixels perform as high-Q resonators only if radiation is not lost into the surrounding environment through scattering and leakage. The photonic crystals rely on total internal reflection and Bragg reflection within the perforated regions of active layer 312 to trap radiation inside the cavity. As a result, radiation loss occurs primarily through scattering (e.g., from lithographic defects) and evanescent coupling to handle substrate 308. Such evanescent coupling can be mitigated, however, by choosing the thickness of BOX layer 310 such that the distance between the photonic crystal and the handle wafer is large—preferably, at least 5 microns to ensure minimal evanescent coupling at the longer wavelengths of the MIR spectrum.

Each detector pixel 324-$i$-$j$-$k$ also includes a pair of metal contacts aligned as thin metal conductors onto the high-Q optical cavities (not shown for clarity). It should be noted that metals do not efficiently absorb radiation in the MIR spectrum and exclude the optical field, which enables resonant cavities with lithographically integrated low-resistance electrical contacts. Further, since detector array 104 is typically arranged such that its metal is on the side of active layer 312 distal to lenses 124, the metal is not in the optical path of the incident light.

Pixels 324 enable detection of MIR radiation in two ways: (a) by generating charge carriers that contribute to conductivity and (b) by generating heat, which can be measured by changes in the conductivity by changing the intrinsic carriers in the material. The first of these is a more efficient method for conversion of radiation to electrical signals. At MIR wavelengths, silicon absorbs radiation and converts it into electron-hole pairs due to the excitation of surface states. It should be noted that in each of pixels 324, the path-length of radiation must be very large to be absorbed because the absorption efficiency in undoped silicon is low. As discussed above, however, this enables the formation of high-Q cavity-enhanced detectors with narrow spectral response. Longer-wavelength radiation (i.e., having lower-energy photons), which is no longer able to excite carriers for photoconduction, are concentrated and trapped in the high-Q optical cavities. It is possible to measure the conductivity of a thermally insulated silicon detector, however, enabling the silicon cavity itself to be used a bolometer, wherein changes in the conductivity of the silicon changes as radiation is absorbed. For an exemplary embodiment of a pixel having a diameter within the range of 30-40 microns, with a Q value of 10,000, the coupling efficiency for radiation having a wavelength of approximately 8 microns is 10%.

In some embodiments, a high voltage is applied across the metal contacts of each detector pixel to induce a high electric field capable of inducing carrier multiplication. Due to the high breakdown voltage of undoped silicon, avalanche gain values within the range of 1 to approximately 1000 can be provided.

As mentioned briefly above, the inclusion of lenses that operate as diffractive optical filters that match the wavelengths in radiation beams 124 with the proper spectrally selective detector elements improves spectral resolution and reduces spectral cross-talk, thereby improving sensitivity.

It should be noted that, due to the fine spectral resolution capability afforded embodiments of the present invention by the hierarchical spectral dispersion system defined by lens arrays 106 and 108, embodiments of the present invention are not limited to a detector array 104 that includes spectrally selective detector pixels, such as pixels 324. As a result, in some embodiments, detector array 104 includes non-spectrally selective detector pixels, such as conventional bolometer elements, conventional MIR detectors, and the like.

Figure 5A:
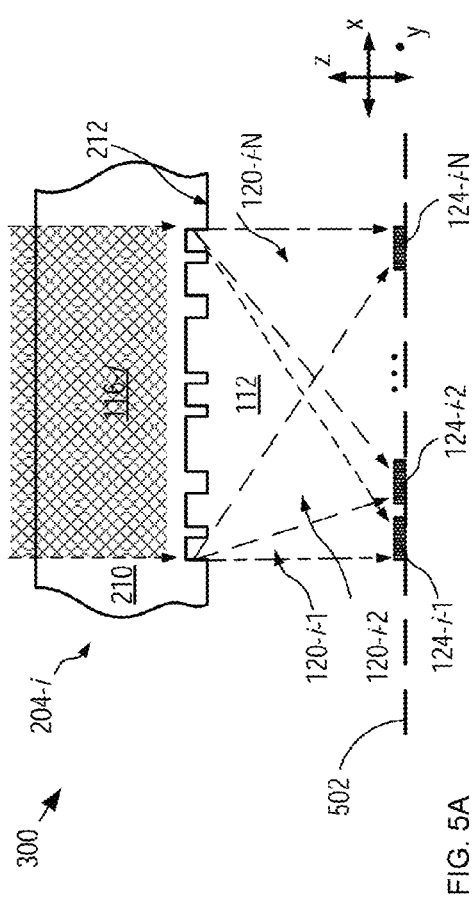
FIG. 5A depicts a schematic drawing of a representative lens 204 of lens array 106.

FIG. 5A depicts a schematic drawing of a representative lens 204 of lens array 106. Lens 204-$i$ is a diffractive focusing lens formed in surface 212 of substrate 210. Lens 204-$i$ receives radiation signal 116-$i$ from emitter 202-$i$ and focuses the radiation as a N spots at focal field 502. Lens array 108 is located at focal field 502; therefore, each focused spot is incident on a different lens 304 of lens array 108. As discussed above, lens 204-$i$ provides radiation beams 120-$i$-1 through 120-$i$-N, each of which includes a different spectral sub-portion of radiation signal 116-$i$. Further, radiation beams 120-$i$-1 through 120-$i$-N take on the absorption characteristics of test sample 112 as they pass through the sample material, giving rise to radiation beams 124-$i$-1 through 124-$i$-N, respectively, which are focused as spots at the lenses of lens array 108. It should be noted that, since radiation signals 116 transit substrate 210, the silicon in the substrate absorbs radiation having wavelengths within its absorption band, thereby providing a spectral filtering functionality.

Figure 5B:
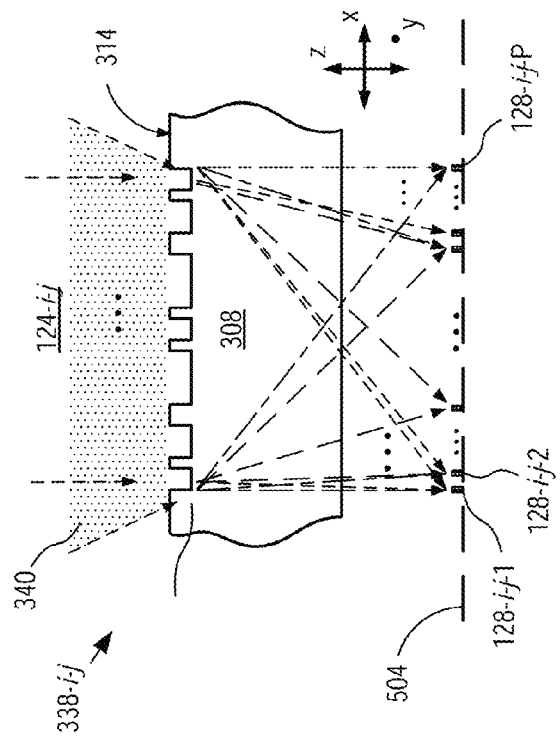
FIG. 5B depicts a schematic drawing of a cross-sectional view of a representative lenslet 338 within a lens 304 of lens array 108.

FIG. 5B depicts a schematic drawing of a cross-sectional view of a representative lenslet 338 within a lens 304 of lens array 108. Lenslet 338-$i$-$j$ is a diffractive focusing lens formed in surface 314 of handle substrate 308. Lenslet 338-$i$-$j$ is operative for receiving a different one of radiation beams 124-$i$-1 through 124-$i$-N, distributing its spectral components into P radiation beamlets (i.e., radiation beamlets 128-$i$-$j$-1 through 128-$i$-$j$-P), and focusing each radiation beamlet as a spot at focal field 504, at which the detector pixels of detector 302-$i$ (as depicted, detector pixels 324-$i$-$j$-1 through 324-$i$-$j$-P) are located. Lenslet 338-$i$-$j$ is designed such that each radiation beamlet 128-$i$-$j$-$k$ is focused to a spot on its corresponding detector pixel 324-$i$-$j$-$k$ (i.e., the detector pixel that is selectively sensitive to the spectral component included in that radiation beamlet).

It should be noted that, as radiation beams 120 transit test sample 112 a portion of their radiation is typically scattered by within the material of the test sample. As a result, the magnitude of the radiation that transits test sample 112 is reduced in a non-wavelength-specific manner, which can obscure the absorption characteristics of the test sample. In addition, the desired spatial separation and distribution of spectral components at detectors 304 is degraded by the random nature of the scattering. This leads to each lens 304-$i$ receiving scattered radiation that includes wavelengths that span the entire MIR spectrum. This scatter in the test sample material, therefore, can lead to significant loss of signal and increased noise, thereby degrading the sensitivity of spectrometer 100.

The present invention mitigates scatter-based issues because each of lenses 304-$i$ has dual functionality. First, each lens provides a primary portion of its respective radiation beamlet 128 to its respective detector pixel, where the primary portion is based solely on the unscattered radiation incident on it (i.e., the radiation contained in the radiation beam 124-$i$-$j$ it receives from test sample 112). Second, the design of the entirety of lens 304-$i$ enables each wavelength component in the scatter radiation received from the test sample to be distributed into a secondary portion of each radiation beamlet such that the primary and secondary portions collectively define the complete radiation beamlet. As depicted in the figures, lens 304-$i$ spatially disperses the spectral components of radiation beam 124-$i$ into radiation beamlets 128-$i$-1 through 128-$i$-N and directs each radiation beamlet to its appropriate pixel 324-$i$-$j$. Each radiation beamlet 128 includes substantially only wavelengths within the spectral range for which its respective pixel 324 is operative. Further, the spectral selectivity of each detector pixel provides substantial immunity to noise due to the receipt of radiation having wavelengths outside of the designed spectral sensitivity of that pixel.

FIGS. 6A-B depict schematic drawings of cross-sectional and perspective views, respectively, of a first spectrometer arrangement in accordance with the present invention. Spectrometer 600 includes emitter array 102, detector module 300, sample chamber 602, and draw tube 604. Spectrometer 600 is a spectrometer system having an integrated sample cuvette.

Emitter array 102 is formed with integrated focusing lenses 204 on substrates 206 and 210, as described above.

Detector array 104 and lens array 106 are formed on substrates 308 and 318, as described above; however, prior to the formation of lens array 106, cavity 606 is formed in surface 314 of substrate 308 to define nascent sample chamber 602. It should be noted that cavity 606 also includes a channel for receiving draw tube 604.

Lens array 106 is then defined in the bottom surface of cavity 606, as described above.

Upon completely of lens array 106, substrates 210 and 308 are joined—preferably via SLID bonding, as described above. The bonding of these substrates seals cavity 606, completing the formation of sample chamber 602.

Sample chamber 602 comprises cavity 606, formed in substrate 308, which is sealed by substrate 210 when substrates 210 and 308 are bonded.

Figure 7:
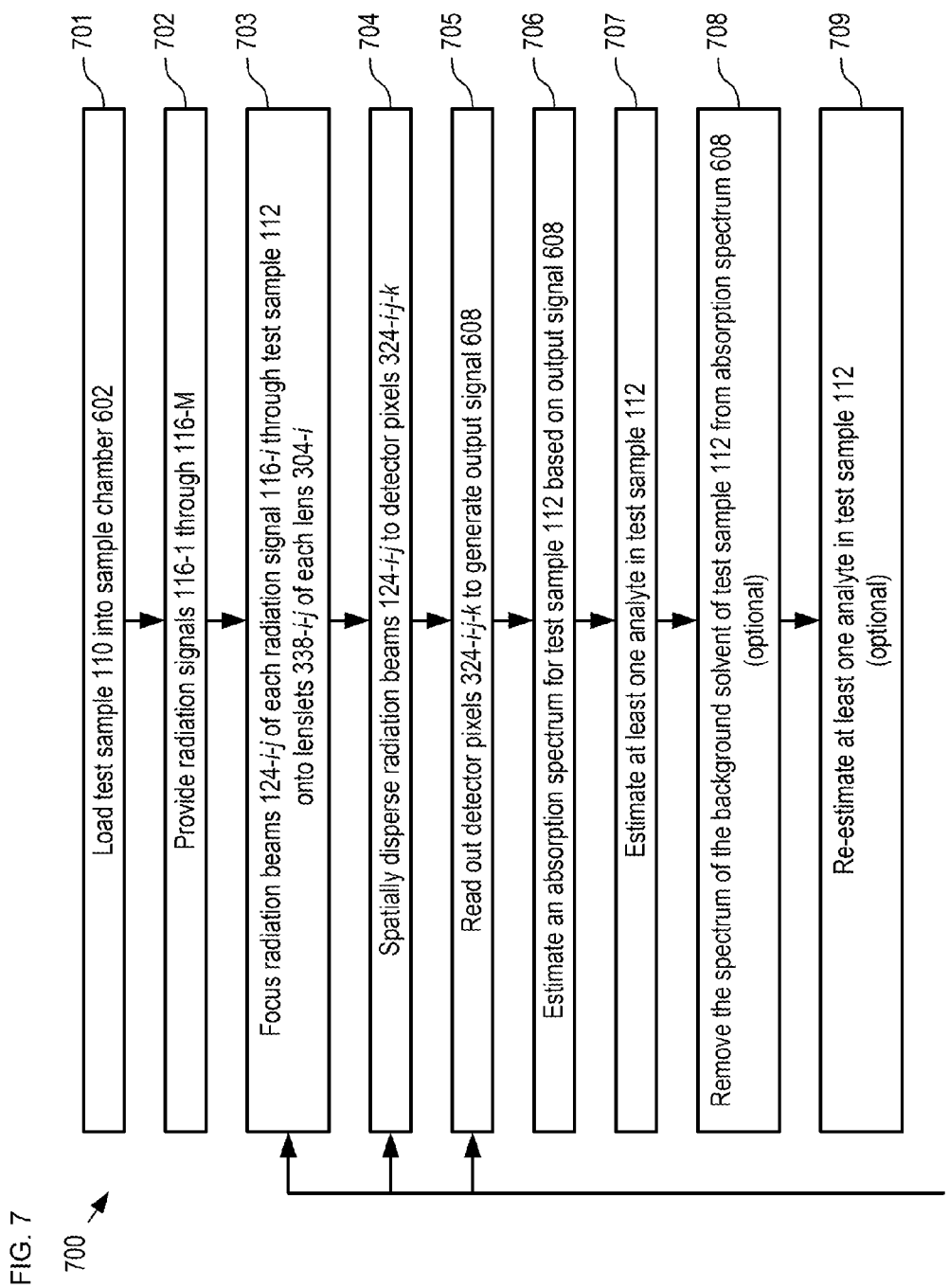
FIG. 7 depicts operations of a method for analyzing a test sample in accordance with the present invention.

FIG. 7 depicts operations of a method for analyzing a test sample in accordance with the present invention. Method 700 is described with reference to spectrometer 600, as well as continuing reference to FIGS. 1-3D and 5A-B. Method 700 begins with operation 701, wherein test sample 112 is loaded into sample chamber 602. In the depicted example, test sample 112 is human blood drawn into sample chamber 602 via draw tube 604.

At operation 702, each emitter 202-$i$, where 1=1 through M, emits radiation signal 116-$i$.

At operation 703, each lens 204-$i$ of lens array 106 spatially disperses the spectral sub-range of its respective radiation signal 116-$i$ into N spectral sub-portions separately contained in radiation beams 120-$i$-1 through 120-$i$-N, each of which is focused through test sample 112 at focal field 502 as radiation beams 124-$i$-1 through 124-$i$-N. Each radiation beam 124-$i$-$j$ is focused onto its corresponding lenslet 338-$i$-$j$ of its corresponding lens 304-$i$ of lens array 108.

At operation 704, each lenslet 338-$i$-$j$ spatially disperses the spectral components in radiation beam 124-$i$ into P spectral components separately contained in radiation beamlets 128-$i$-$j$-$k$ and directs the radiation beamlets to detector pixels 324-$i$-$j$-$k$.

At operation 705, each detector pixel 324-$i$-$j$-$k$ is read out to detect the intensity of its received radiation beamlet 128-$i$-$j$-$k$. The detector responses from pixels 324 are provided to processor 110 as output signal 608.

It is another aspect of the present invention that the response of pixels 324 can be read out in two different ways—differential and pulsed measurements. Each pixel reading preferably includes both a resistance measurement of the high-Q resonator of that pixel, and a resistance measurement of "blind" pixel comprising a low-Q resonator with similar geometry and thermal mass. These two resistance readings enable a differential measurement that mitigates deleterious effects of environmental drift. They also enable recalibration of the filtered detectors without the need for a mechanical shutter. Since the detector resistivity changes slowly, it preferable to use pulsed measurements to reduce the influence of the measurement current on the pixel reading. Pulsed measurement provides readings that are determined by the carrier lifetime of electrons in the silicon detector region. For the most sensitive detector performance, the conductivity of the silicon is preferably as low as possible, and the absorption of MIR radiation in the surrounding material is substantially minimized. As a result, interference from spectrally non-specific background "noise" can be reduced, improving SNR. It should be noted that reading out pixels 324 using a pulsed approach also reduces the exposure of biological tissue to high-energy radiation, enabling the use of embodiments of the present invention in applications where prior-art MIR spectrometers are undesirable.

Further, the application of a high electric field across a detector pixel, as described above, leads to an increase in the temperature of the pixel due to resistive heating. Using pulsed measurement of the pixels mitigates this problem as well. In addition, by performing two measurements during each pulse period, one with the high field applied and the other with the high field off, the detector pixel temperature and the photoconductance can be measured independently. This enables the confirmation of the higher-speed carrier-based measurement with a bolometric background measurement, which enables further-improved SNR and, therefore, detector sensitivity.

At operation 706, processor 110 estimates an absorption spectrum for test sample 112 based on output signal 608.

At operation 707, processor 110 detects at least one analyte in test sample 112 based on the estimated absorption spectrum. In some embodiments, detecting an analyte means merely identifying its presence. In some embodiments, detecting an analyte also includes estimating its concentration in the test sample.

It should be noted that the present invention is particularly well suited for the analysis of test samples that include one or more analytes suspended or dissolved in a background solvent or carrier medium. As discussed in U.S. Pat. No. 8,344,323 and U.S. Patent Publication No. 20130075614, each of which is incorporated herein by reference in their entirety, identifying and/or quantifying analytes in a background solvent using MIR radiation can be extremely difficult because many solvents (e.g., water) are particularly absorbing in the MIR range. As a result, it can be difficult to obtain measurement signals of sufficient magnitude to assure a suitable SNR. By using the background solvent itself as a wavelength reference, however, the spectral signature of the background solvent can be substantially removed from a composite spectrum based on the complete chemistry of the sample. As a result, the spectral features associated with an analyte in the sample can be more easily identified. Further, an estimation of the concentration of the analyte can be developed by normalizing the spectral characteristics of the analyte to the spectral characteristics of the background solvent, which can, in some cases, provide an absolute wavelength reference.

The ability to use some background solvents as absolute wavelength references arises from the fact that certain chemicals exhibit temperature invariant behavior that is linked to specific wavelength characteristics. Water is one such chemical. In water, for example, molecular vibrations due to the nature of the bonds within a water molecule, and mediated by the molecular structure, gives water a distinct spectra comprising temperature-invariant features. By registering an absorption spectrum measured for a sample solution to these known features, the known, characteristic absorption spectrum of water can be computationally removed from a measured composite spectrum, thereby isolating and identifying the spectral characteristics of each of the analytes included in the sample solution.

As a result, in some embodiments, method 700 includes optional operations 708 and 709, wherein the known spectrum of the background solvent of test sample is removed from the estimated absorption spectrum for test sample 112 and the presence/concentration of the at least one analyte is re-estimated.

Figure 8A:
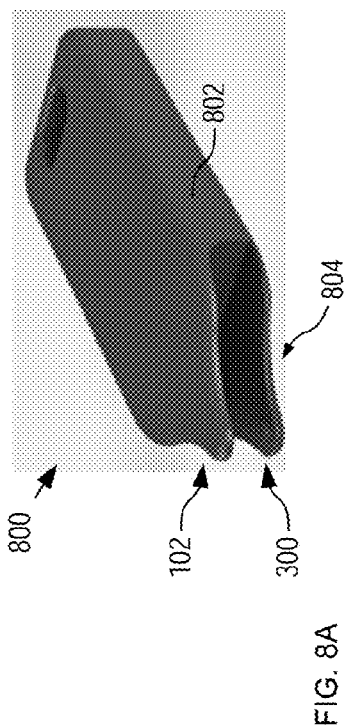
FIGS. 8A-B depict schematic drawings of perspective and cross-sectional views of a second spectrometer arrangement in accordance with the present invention.
Figure 8B:
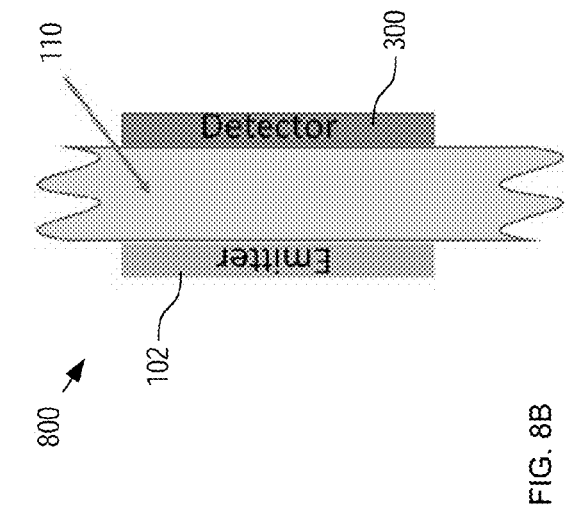

FIGS. 8A-B depict schematic drawings of perspective and cross-sectional views of a second spectrometer arrangement in accordance with the present invention.

Spectrometer 800 is analogous to spectrometers 100 and 600, as described above; however, in spectrometer 800, emitter array 102 and detector module 300 are disposed on opposing jaws of pincher 804.

Pincher 804 comprises a pair of flexible members that extend from housing 802 to define a gap between them. As depicted in FIG. 8B, a test sample, such as a tissue sample, can be placed into the gap of pincher 804 and clamped in place by simply applying pressure to the jaws.

Figure 9:
FIG. 9 depicts spectrometer 800 in a measurement position for the non-invasive measurement of blood chemistry by interrogating a region of webbing between two fingers of a test subject.

FIG. 9 depicts spectrometer 800 in a measurement position for the non-invasive measurement of blood chemistry by interrogating a region of webbing between two fingers of a test subject.

FIG. 10 depicts a schematic drawing of a cross-sectional view of a third spectrometer arrangement in accordance with the present invention. Spectrometer system 1000 is a two-part system comprising docking station 1002 and sample cuvette 1004.

Docking station 1002 is analogous to system 100 described above; however, receiver 1002 includes receiver 1006 for locating sample cuvette 1004 between lens arrays 106 and 108. In some embodiments, receiver 1006 includes stand-offs, or similar structures, for locating sample cuvette 1004 such that it is separated from the interior surfaces of the receiver by a set spacing.

Sample cuvette 1004 is a sample holder that includes body 1008 and sample chamber 602. Body 1008 comprises a material that is substantially transparent for MIR radiation, such as float-zone silicon, silver halide, etc. Sample chamber 602 is formed using conventional MEMS-based fabrication processes, such as those described above.

Typically, sample cuvette 1004 includes a draw tube (not shown) for loading test sample 112 into chamber 602; however, one skilled in the art will recognize that test sample 112 can be loaded into chamber 602 in myriad ways, such as via a syringe, pipette, capillary force, etc.

Since sample cuvette 1004 does not include electronics, optics, emitters, or detectors, and since it can be made using extremely low-cost materials and processes, it is substantially disposable. As a result, system 1000 enables high sensitivity, high-volume spectroscopy applications at lower cost than prior-art MIR spectrometers.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A mid-infrared (MIR) spectroscopy system for detecting an analyte in a test sample, the spectroscopy system comprising:
   (1) a hierarchical spectral dispersion system comprising:
      (a) a first plurality of lenses arranged to receive a plurality of radiation signals, each having a different first spectral range, the plurality of first spectral ranges collectively spanning at least a portion of the MIR spectrum, each lens of the first plurality thereof being operative for receiving a different radiation signal of the plurality thereof and distributing it into a plurality of radiation beams focused at a first focal field after interacting with the test sample, wherein each radiation beam has a second spectral range that is smaller than the first spectral range, and wherein the plurality of second spectral ranges is collectively equal to the first spectral range; and (b) a second plurality of lenses located at the first focal field, each lens of the second plurality thereof being operative for receiving a different radiation beam of the plurality thereof and distributing it into a plurality of radiation beamlets focused at a second focal field, wherein each radiation beamlet has a different third spectral range that is smaller than the second spectral range of its respective radiation beam, and wherein the plurality of third spectral ranges is collectively equal to the second spectral range; and (2) a first plurality of detector pixels located at the second focal field, the first plurality of detector pixels being arranged such that each detector pixel receives a different radiation beamlet of the plurality thereof;

wherein the plurality of first spectral ranges collectively spans the MIR spectrum.

2. The spectroscopy system of claim 1 wherein a first detector pixel of the first plurality thereof is substantially spectrally selective for the third spectral range of the radiation beamlet it receives.

3. The spectroscopy system of claim 2 wherein the first detector pixel comprises a first material that is substantially transparent for MIR radiation, the first detector pixel including a first arrangement of features that collectively defines a photonic crystal, wherein the size and spacing of the features are based on the third spectral range of the radiation beamlet it receives.

4. The spectroscopy system of claim 3 wherein the first material is float-zone silicon.

5. The spectroscopy system of claim 3 wherein the features are dimensioned and arranged to give rise to surface states that enable the absorption of MIR radiation and the generation of charge-carriers in the first material.

6. The spectroscopy system of claim 5 wherein the first pixel includes first and second contacts that are operative for inducing avalanche gain in the first material.

7. The spectroscopy system of claim 1 further comprising a first detector comprising a second plurality of detector pixels that is collectively spectrally selective for a first radiation signal of the plurality thereof, the first plurality of detector pixels including the second plurality of detector pixels, wherein the second plurality of pixels includes a first detector pixel and a second detector pixel, and wherein the first detector pixel is substantially spectrally selective for the third spectral range of the radiation beamlet it receives and the second detector pixel is a blind pixel.

8. The spectroscopy system of claim 1 further comprising (3) a plurality of emitters, each emitter of the plurality thereof emitting a different radiation signal of the plurality thereof.

9. The spectroscopy system of claim 8 wherein a first emitter of the plurality thereof comprises a filament that is dimensioned and arranged to emit a first radiation signal of the plurality thereof, the filament including a plurality of emitting elements characterized by a first emitter width and first emitter spacing, the first emitter width and first emitter spacing being based on the first spectral range of the first radiation signal.

10. The spectroscopy system of claim 9 wherein the first emitter further comprises a mirror, the mirror and the filament collectively defining a resonant cavity having a cavity length that is based on the first spectral range of the first radiation signal.

11. The spectroscopy system of claim 1 wherein a first lens of the second plurality thereof distributes its respective radiation beamlets such that they are focused at a first plurality of spots at the second focal field, and wherein the first lens is dimensioned and arranged to focus scatter radiation received from the test sample at a second plurality of spots on the second focal field, wherein the first plurality of spots and second plurality of spots are each arranged such that each spot is uniquely characterized by a different third spectral range of the plurality thereof.

12. The spectroscopy system of claim 1 further comprising (3) a sample cuvette for holding the test sample, wherein the sample cuvette includes the first plurality of lenses, the second plurality of lenses and the plurality of detector pixels.

13. The spectroscopy system of claim 1 further comprising:

(3) a docking station, the docking station including a receiver for receiving a sample cuvette, the first plurality of lenses, the second plurality of lenses and the plurality of detector pixels; and (4) the sample cuvette for holding the test sample, wherein the sample cuvette includes:

(a) a body comprising a first material that is substantially transparent for MIR radiation; and (b) a sample chamber for locating the test sample;

wherein the sample cuvette is dimensioned and arranged to be removably located within the receiver.

14. A hyperspectral spectroscopy system comprising:

a hierarchical spectral dispersion system that is dimensioned and arranged to distribute the spectral components of a first plurality of radiation signals into a plurality of radiation beamlets, the first plurality of radiation signals collectively spanning a first spectral range that is at least a portion of the mid-infrared (MIR) spectrum, and each radiation beamlet including a different spectral component included in the first spectral range such that the plurality of spectral components collectively spans the first spectral range, each spectral component having a second spectral range that is smaller than the first spectral range; and a plurality of detectors, each detector including a plurality of detector pixels, and each detector pixel being spectrally selective such that it detects only one spectral component of the plurality thereof;

wherein the hierarchical spectral dispersion system and the plurality of detectors are arranged such that each radiation beamlet of the plurality thereof is directed to the detector pixel that is spectrally selective for its respective spectral component.

15. The spectroscopy system of claim 14 wherein the hierarchical spectral dispersion system includes:

a plurality of first lenses, each first lens being arranged to distribute a different radiation signal of the first plurality thereof into a plurality of radiation beams, each radiation beam having a third spectral range that is smaller than the first spectral range and larger than the second spectral range; and a plurality of second lenses, each second lens including a plurality of lenslets, and each lenslet being arranged to receive a different radiation beam of the plurality thereof and distribute it into a different radiation beamlet of the plurality thereof.

16. The spectroscopy system of claim 14 wherein a first detector is spectrally selective for a first radiation signal of the plurality thereof, and wherein a first detector pixel of the first detector is substantially spectrally selective for a first spectral component of the first radiation signal, and further wherein a second detector pixel of the first detector is a blind pixel.

17. The spectroscopy system of claim 14 wherein a first detector pixel of a first detector of the plurality thereof comprises a first material that is substantially transparent for MIR radiation, the first detector pixel including a first arrangement of features that collectively defines a photonic crystal, wherein the size and spacing of the features are based on the spectral component of the radiation beamlet it receives.

18. The spectroscopy system of claim 14 further comprising a plurality of emitters, each emitter being operative for providing a different radiation signal of the first plurality thereof.

19. The spectroscopy system of claim 18 wherein a first emitter of the plurality thereof comprises a filament that is dimensioned and arranged to emit a first radiation signal of the plurality thereof, the filament including a plurality of emitting elements characterized by a first emitter width and first emitter spacing, the first emitter width and first emitter spacing being based on the first spectral range of the first radiation signal.

20. The spectroscopy system of claim 19 wherein the first emitter further comprises a mirror, the mirror and the filament collectively defining a resonant cavity having a cavity length that is based on the first spectral range of the first radiation signal.

21. A method for analyzing a test sample, the method comprising:
distributing each of a first plurality of radiation signals into a first plurality of radiation beams, each radiation signal being characterized by a different first spectral range such that the plurality of first spectral ranges collectively spans at least a portion of the MIR spectrum;
focusing each radiation beam of the first plurality thereof at a first focal field such that the first plurality of radiation beams interacts with the test sample to give rise to a second plurality of radiation beams whose spectral content is based on the chemical composition of the test sample, wherein each radiation beam of the second plurality thereof has a different second spectral range that is smaller than the first spectral range of its respective radiation signal, and wherein each plurality of second spectral ranges collectively spans the first spectral range of its respective radiation signal;
distributing each radiation beam of the second plurality thereof into a plurality of radiation beamlets that are focused at a second focal field, each radiation beamlet having a spectral component characterized by a different third spectral range that is smaller than the second spectral range of its respective radiation beam of the second plurality thereof, and wherein each plurality of third spectral ranges collectively spans the second spectral range of its respective radiation beam of the second plurality thereof;
detecting the plurality of radiation beamlets at a plurality of detectors located at the second focal field, wherein each detector provides an output signal based on respective radiation beamlet; and
detecting at least one analyte in the test sample based on the plurality of output signals.

22. The method of claim 21 further including providing the plurality of detectors such that each detector is non-spectrally selective radiation.

23. The method of claim 21 further including:
providing a first detector of the plurality thereof such that the first detector is spectrally selective for the spectral component of a first beamlet of the plurality thereof; and
focusing the first beamlet at the first detector.

24. The method of claim 21 further including providing a first detector of the plurality thereof such that the first detector comprises:
a first material that is substantially transparent for MIR radiation; and
a first arrangement of features that collectively defines a photonic crystal, wherein the size and spacing of the features are based on the spectral component of the radiation beamlet it receives.

25. The method of claim 24 further including:
providing a second detector of the plurality thereof such that the second detector is a blind detector; and
comparing a first output signal provided by the first detector and a second output signal provided by the second detector.

26. The method of claim 24 further including reading out the first detector by operations comprising:
providing an electric field across the first detector during a first portion of a pulse period;
providing no electric field across the first detector during a second portion of the pulse period;
measuring the photoconductance of the first pixel during the first portion; and
measuring the temperature of the first pixel during the second portion.

27. The spectroscopy system of claim 21 further comprising:
providing a plurality of emitters, each emitter being operative for selectively emitting a different radiation signal of the first plurality thereof; and
enabling each of the plurality of emitters to emit its respective radiation signal.

28. The spectroscopy system of claim 27 wherein the plurality of emitters are energized one at a time.

29. The spectroscopy system of claim 27 wherein a first emitter of the plurality thereof is provided such that it comprises a filament that is dimensioned and arranged to emit a first radiation signal of the first plurality thereof, the filament including a plurality of emitting elements characterized by a first emitter width and first emitter spacing, the first emitter width and first emitter spacing being based on the first spectral range of the first radiation signal.

30. The spectroscopy system of claim 29 wherein the first emitter is provided such that it further comprises a mirror, the mirror and the filament collectively defining a resonant cavity having a cavity length that is based on the first spectral range of the first radiation signal.

* * * * *